United States Patent [19]

Katayama et al.

[11] Patent Number: 5,138,038

[45] Date of Patent: Aug. 11, 1992

[54] PROTEIN PARTIAL DEGRADATION PRODUCT, PROCESS FOR PREPARING IT AND ITS USE

[75] Inventors: Sakae Katayama, Osaka; Atsushi Tsuda, Takatsuki; Kenzi Hanno, Hirakata, all of Japan

[73] Assignee: Katayama Chemical Works Co., Ltd., Osaka, Japan

[21] Appl. No.: 593,289

[22] Filed: Oct. 4, 1990

Related U.S. Application Data

[63] Continuation of Ser. No. 215,727, Jul. 6, 1988, abandoned.

[30] Foreign Application Priority Data

| Jul. 6, 1987 | [JP] | Japan | 62-168336 |
| Jul. 27, 1987 | [JP] | Japan | 62-188639 |
| Feb. 5, 1988 | [JP] | Japan | 63-26239 |
| May 6, 1988 | [JP] | Japan | 63-110905 |

[51] Int. Cl.$^5$ .............................. A23J 3/30; A23J 3/14; A23J 3/16
[52] U.S. Cl. .................................. 530/343; 530/372; 530/374; 530/378; 252/89.1; 426/656; 435/68.1
[58] Field of Search ............... 530/343, 372, 374, 378, 530/375

[56] References Cited

U.S. PATENT DOCUMENTS

| 1,245,983 | 11/1917 | Satow . |
| 2,090,537 | 11/1936 | Lund . |
| 2,119,872 | 6/1938 | Wiegand . |
| 2,232,052 | 2/1941 | Cummins . |
| 2,258,260 | 10/1941 | Rice . |
| 2,271,499 | 1/1942 | Rice . |
| 2,431,256 | 11/1947 | Keil . |
| 2,434,874 | 1/1948 | Tucker et al. . |
| 2,513,351 | 7/1950 | Olcott et al. . |
| 2,582,965 | 1/1952 | Coffman . |
| 3,127,388 | 3/1964 | Johnson . |
| 3,394,119 | 7/1968 | Luce et al. . |
| 3,928,630 | 12/1975 | Perini . |
| 3,932,671 | 1/1976 | Yokotsuka et al. . |
| 4,100,024 | 7/1978 | Adler-Nissen . |
| 4,100,151 | 7/1978 | Adler-Nissen . |
| 4,324,805 | 4/1982 | Olsen . |
| 4,443,540 | 4/1984 | Chervan . |
| 4,687,739 | 8/1987 | Sugisawa et al. ............ 530/378 |
| 4,771,126 | 9/1988 | Hirotsuka et al. . |

Primary Examiner—Howard E. Schain
Assistant Examiner—Susan M. Perkins
Attorney, Agent, or Firm—Bryan, Cave, McPheeters & McRoberts

[57] ABSTRACT

Novel protein partial degradation products obtainable from grain proteins such as wheat protein, maize protein, soya bean protein, etc., by specific degradation treatments, which are useful as a quality-improving agent for various food stuffs, a surface active agent, a dispersing agent for particles, etc.

8 Claims, 5 Drawing Sheets

PROTEIN PARTIAL DEGRADATION PRODUCT, PROCESS FOR PREPARING IT AND ITS USE

This is a continuation of U.S. application Ser. No. 215,727 filed Jul. 6, 1988, now abandoned.

BACKGROUND OF THE INVENTION

1. Field of the Invention

The present invention relates to a protein partial degradation product, a process for preparing it, and its use. More particularly, it relates to a novel protein partial degradation product obtained by degradation of a grain protein such as wheat protein, maize protein, soya bean protein, etc., a process for preparing the protein partial degradation product and it use as a quality-improving agent for food stuffs or a surface active agent.

2. Description of the Prior Art

Hitherto, as partial degradation products of vegetable proteins, there has been known those hydrolyzed by an acid, alkali or enzyme. Further, it has been known that such partial degradation products could be obtained also by an oxidative degradation using an oxidizing agent or a reductive degradation using a reducing agent.

For instance, Ian L. Batey et al. reported on the properties and the amino acid composition of partial hydrolyzates of wheat gluten obtained by hydrolysis with an alkali or acid ("Preparation of Salt-Free Protein Products from Acid or Alkali-Treated Proteins", Food Chemistry No. 12 (1983), Pages 265-275). On the other hand, A. M. Hermansson et al. reported that partial hydrolyzates of rapeseed oil protein obtained by hydrolysis with an alkali, acid or enzyme show some degrees of solubility in water, emulsifying and forming properties ("Functional Properties of Proteins for Foods - Modification Studies on Rapeseed Protein Concentrate", Lebensmittel - Wissenschaft und - Technologie Vol. 7, No. 3 (1974), Pages 176-181).

In Japanese Unexamined Patent Publication No. Sho 50-95443, it is disclosed that the slightly acidic gluten powder obtained from wheat gluten with its acidifying treatment at pH 2.0-6.0 is superior, as an additive for food stuffs, to one obtained by treatment with a reducing agent. This Publication, however, does not disclose any specific effect of the powder as the additive. Further, it is disclosed in Japanese Unexamined Patent Publication No. Sho 60-237939 that a wheat gluten partial hydrolyzate is obtained by hydrolysis of wheat gluten with an enzyme can be used as a substitute for caseinates in the production of imitations of cheese.

In Japanese Unexamined Patent Publication No. Sho 53-124654, there is disclosed a process for the production of processed meat by addition of a gluten hydrolyzate, which is obtained under an acidic condition with hydrochloric acid, in the form of powder.

On the other hand, it is described in Japanese Unexamined Patent Publications No. Sho 56-8665 and No. Sho 57-79849 that partial degradation products of a protein, obtained by hydrolysis with an acid or an enzyme, have a surface activate capacity.

Besides, it has been known that hydrolyzates of a protein obtained by hydrolysis with an enzyme is useful for the stabilization of whipped dessert-type products (U.S. Pat. No. 3,889,001 and U.S. Pat. No. 3,903,310).

Further, it has been reported recently that a gluten partial hydrolyzate obtained by treating wheat gluten with a pepsin-immobilized bioreactor can be utilized for improving quality on baking cake and bread such as sponge cake (A Japanese paper "Kagaku Kogyo Jiho" issued on Jun. 25, 1987).

Thus, various investigation reports have been made as to partial hydrolyzates of vegetable proteins, and in some of them there have been given disclosures on the emulsifying capacity and the quality-improving capacity for food stuffs of the partial hydrolyzates reported therein. However, according to the result of our confirmation tests, any of the partial degradation products obtained by subjecting a representative grain protein such as wheat protein, maize protein, soya been protein, etc. to either of the above-mentioned degradation means could be used as a quality-improving agent for food stuffs or a surface active agent, but its capacity was not of satisfactory level.

On the other hand, polyhydric alcohol/fatty acid ester type surface active agents and lecithin are known as relatively safe surface active agents, and they are used in the fields of food industry and medical treatment, particularly, used widely as a quality-improving agent for food stuffs.

For instance, the so-called polyhydric alcohol/fatty acid ester type surface active agents, such as glycerol/fatty acid ester, propylene glycol/fatty acid ester, sucrose/fatty acid ester etc. are widely used as a qualityimproving agent for starchy food such as bread or noodle, as the case may be, in combination with ascorbic acid or a gluconolactone (Japanese Patent Publication No. Sho 56-42887, Japanese Unexamined Patent Publications No. Sho 55-118334 and No. Sho 55-118335). Further, it is also proposed to use the glycerol/fatty acid ester, after subjecting it to a specific treatment (Japanese Patent Publication No. Sho 59-41379).

Glycerol/fatty acid ester and sucrose/fatty acid ester are frequently used as a quality-improving agent for animal proteinic food stuffs using fish or meat as the main material, such as boiled fish paste, ham, sousage, hamburger, fried ball of mincemeat, etc., and also for vegetable proteinic food stuffs using soya bean protein, wheat gluten and the like as the main material, such as bean-curds, etc. (Japanese Unexamined Patent Publication No. Sho 53-79058, No. Sho 43-8685 and No. Sho 58-89146).

Polyhydric alcohol/fatty acid ester type surface active agents and lecithin are widely used as a qualityimproving agent for creamy processed milk products such as coffee whitener, whip cream, ice cream, etc. (Japanese Patent Publications No. Sho 54-39459 and No. Sho 51-9823).

Further, polyhydric alcohol/fatty acid ester type surface active agents and lecithin are used as a qualityimproving agent or emulsion-stabilizer for water-in-oil emulsion type food stuffs such as margarine, shortening, etc., and oil-in-water emulsion type food stuffs such as dressing, etc. (Japanese Patent Publications No. Sho 51-17150 and No. Sho 57-58898).

However, the above-described surface active agents, polyhydric alcohol/fatty acid esters and the like, are chemical synthetic products in themselves and accordingly are uncertain in respect of their toxicity, although they are approved as food additives. Moreover, these surface active agents are not necessarily satisfactory in respect of the cost and the effect of quality-improving.

Under such circumstances, we have made various investigations and have found the fact that a hydrolyzate obtained by a two or more-step degradation treatment consisting of a combination of an indispensable hydrolysis treatment with alkali by conventional means with one or more degradation treatments with any of acid, enzyme, oxidizing agent and reducing agent (i) is novel which is different from known hydrolyzates and (ii) has a surface activate capacity such as an emulsifying capacity or a surface tension-reducing capacity, and a quality-improving capacity for food stuffs, which are significantly superior to those of known hydrolyzates and equal to, or higher than, those of the above-mentioned sucrose/fatty acid esters or lecithin, and further a good particles-dispersing capacity.

SUMMARY OF THE INVENTION

Thus, the present invention provides a protein partial degradation product which is obtained from a grain protein and is characterized by the following properties:

(a) its weight average molecular weight (according to the Gel filtration method) is in the range of 500-90000, (b) its ultraviolet absorption $\lambda$max is found near 260-280 nm, and its infrared absorption is found near 1400, 1630 and 3400 $cm^{-1}$, (c) its isoelectric point is in the range of pH 3.9-5.0, (d) it has a buffer action (2-25 ml of 1N-hydrochloric acid is required for lowering the pH of 100 ml of its 5% (by weight) aqueous solution from 6 to 2), (e) it is soluble in water and insoluble in methanol, ethanol, acetone and ethyl ether, (f) its appearance is pale yellow - red brown colored powder, (g) it shows coloration in Xanthoprotein reaction and Ninhydrin reaction, (h) it has a potent, surface tension-reducing capacity (the surface tension of pure water at 25° C. is reduced to 50 dyne/cm or less (measured with du Noüy's tensiometer), by adding 0.1% (by weight) of it to the pure water), and (i) it has a potent emulsifying capacity (100 g of a mixture of water and soya bean oil, containing at least 30% (by weight) of soya bean oil, can be emulsified completely, by adding 1 g of it to the mixture), The protein partial degradation products as specified above are believed to be per se new substances, which are not described in any literature issued prior to the present invention.

Besides, the above-mentioned molecular weight was determined according to the Gel filtration method using sodium polystyrenesulfonate having a molecular weight of 1600, 6500, 16000, 65000 or 88000, as the standard substance, and Sephadex G-75 or G-100 (from pharmacia Ltd.) as the carrier.

BRIEF EXPLANATION OF THE DRAWINGS

FIGS. 2a, 1b, 3a, 3b, 4a, 4b, 5a and 5b are graphs each showing an optical characteristic of a partial degradation product of the present invention, wherein FIGS. 2a, 3a, 4a and 5a each shows a UV light and visible light absorption spectrum and FIGS. 2b, 3b, 4b and 5b each shows an IR light absorption spectrum.

DETAILED DESCRIPTION OF THE PREFERRED EMBODIMENT

Figure 1A:
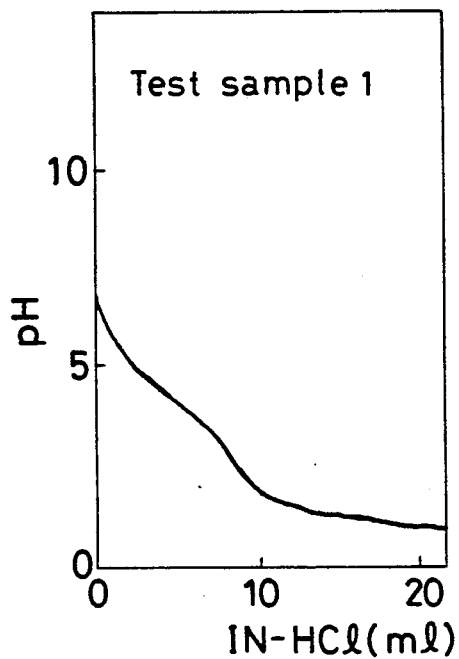
FIGS. 1a, 1b, 1c and 1d are graphs each showing a pH-HCl curve of a partial degradation product of the present invention.

The most characteristic property of the protein partial degradation products of the present invention, which differentiates them from hitherto known protein partial degradation products, is their emulsifying property. That is, the partial degradation products of the present invention have an excellent emulsifying capacity which is able to emulsify 100 g of a mixture of water and soya bean oil, containing at least 30% (by weight) of soya bean oil, completely, by adding 1 g of them to the mixture. The term "at least" used here means that 100 g of the mixture containing more than 30% (by weight),for example, 40% (by weight) or 50% (by weight), of soya bean oil can be emulsified completely, and the "complete emulsification" means that a uniformly emulsified state is maintained for 10 minutes or more, preferably for 1 hour or more, as the mixture is left to stand at room temperature after the emulsifying treatment by stirring or the like. Any partial degradation product known hitherto does not have such a remarkable emulsifying capacity. Therefore, the partial degradation products of the present invention are evidently differentiated from the partial degradation products known thereto, at least in this respect.

By the way, such protein partial degradation products of the present invention contain 0.02-4% (by weight) of amide type nitrogen and 0.2-2% (by weight) of amino type nitrogen.

In the present invention, the term "grain protein" means a protein contained in grain, and the "grain" here means the seed of wheat and barley, corns (for example, maize), beans (for example, soya beans) and the like. Among proteins contained in such grains, wheat protein contains glutenin and gliadin as the main components and is usually called wheat gluten, and maize protein contains zein as the main component and is usually called maize gluten. They each are a known substance which can be obtained from the corresponding grain by separation and extraction according to the usual manner. For example, to obtain wheat protein (wheat gluten), wheat flour is kneaded stiffly by adding a small amount of water and then kneaded in a large amount of water whereby starch is suspended in water and the gluten-containing portion remains as a sticky lump. By repeating this operation several times while replacing the water with new one, wheat protein is obtained as a grayish brown sticky lump. For the preparation of the partial degradation products of the present invention, although such lump can be used as it is, a product obtained by drying, further purifying or partial modifying of the lump may also be used. Wheat gluten is commercially available in the form of dry powder. Other commercially available maize gluten, soya bean protein, etc. may also be used in convenience.

These proteins may be used in the form of either crude products or purified products. However, it is preferable to use a product containing the protein in an amount of 70% or more.

The partial degradation products of the present invention can be prepared by subjecting the above-mentioned grain protein to a multistep degradation treatment consisting of a combination of a hydrolysis treatment with alkali with one or more degradation treatments with any of acid, enzyme, oxidizing agent and reducing agent. That is, the partial degradation products are obtained by combining a degradation treatment with alkali with other degradation treatment(s).

The above hydrolysis treatment with alkali is suitably effected by heating the subject in a dilute aqueous alkaline solution. Usually, it is suitable to heat an aqueous solution or dispersion of the subject to be hydrolyzed at ca. 60°–180° C. for ca. 10–600 minutes while stirring in the presence of an alkaline agent such as sodium hydroxide, potassium hydroxide, calcium hydroxide, sodium carbonate, potassium carbonate, etc. As the aqueous solution or dispersion of the subject to be hydrolyzed, one containing 2–40% (by weight) of the subject is preferably used. The amount of an alkaline agent used is preferably 0.1–6 g per 20 g of the subject to be hydrolyzed.

Among other degradation treatments to be effected in combination with the above-mentioned hydrolysis treatment with alkali, the degradation treatment with acid is suitably effected by heating the subject in a dilute aqueous acid solution. Usually, it is suitable to heat an aqueous solution or dispersion of the subject to be degraded at ca. 60°–120° C. for ca. 10–600 minutes while stirring in the presence of an inorganic acid such as hydrochloric acid, sulfuric acid, etc. or an organic acid such as acetic acid or the like. The quantitative conditions here are preferably the same as those mentioned above for the alkaline hydrolysis.

The degradation treatment with enzyme is suitably effected in a dilute aqueous solution of an enzyme having protease activity. Usually, it is effected by keeping an aqueous solution or dispersion of the subject to be degraded at ca. 10°–60° C. for ca. 60–600 minutes in the presence of a small amount of an enzyme such as pepsin, alkali protease, papain, etc. under the optimal pH condition for the enzyme. The quantitative conditions here are preferably the same as those described above, except that 0.02–5 g of the enzyme is used per 20 g of the subject to be degraded.

The degradation treatment with reducing or oxidizing agent is suitably effected in a dilute aqueous solution of the reducing or oxidizing agent. Usually, it is effected by keeping an aqueous solution or dispersion of the subject to be degraded at ca. 10°–100° C. for ca. 10–600 minutes in the presence of a small amount of a reducing agent such as a sulfite, a thiol compound, erysorbic acid, hydrazine, etc. or an oxidizing agent such as hydrogen peroxide, a hypochlorite, etc. The quantitative conditions here are preferably the same as those described above, except that 0.1–5 g of the reducing agent or the oxidizing agent is used per 20 g of the subject to be degraded.

There is no limitation in the order of effecting the above-mentioned multiple degradation treatments. That is, the partial degradation products of the present invention can be obtained by subjecting the starting material such as wheat gluten or the like, first to the hydrolysis treatment with alkali (A) and thereafter to one or more of the degradation treatments with acid, enzyme, reducing agent or oxidizing agent (degradation treatments with an agent except alkali (B) or, in reverse order, first to (B) and then to (A . Further, they can be obtained also by subjecting first to a degradation treatment with an agent except alkali (B), thereafter to the hydrolysis treatment with alkali (A), and again to a degradation treatment with an agent except alkali (B). Neutralization treatment may suitably be effected between these treatments.

It has been found that the partial degradation products of the present invention thus obtained are high molecular amphoteric electrolytes having various interesting properties and actions.

First, it has been confirmed that the partial degradation products have especially potent surface-activate capacity and particle (inclusive of solid particle and liquid particle) dispersing capacity. In addition, they are considered to have an adsorbing capacity onto particle surface, complex-forming capacity with protein and starch, and the like. Such properties and use of the partial degradation products are explained hereinafter.

(i) They are useful as a surface active agent, mainly because of their surface-activate capacity. They have a high HLB and hydrophilic property, in addition to their high surface-activate capacity, and are low foaming. They have the advantage of low toxicity, low price, etc. because they are a kind of modified food stuffs.

There is no special limitation in the fields where they are used as a surface active agent. They can be used in various fields such as food stuffs, cosmetics, pharmaceutical medicines, agricultural chemicals, etc. Particularly, on the ground of their high HLB, they are useful as a detergent or a solubilizer. For example, they can be used also as a solubilizer for conventional surface active agents less soluble in water, such as polyhydric alcohol/fatty acid ester type surface active agents, or lecithin.

(ii) They are useful as a dispering agent for various particles in the fields of food stuffs, cosmetics, agricultural chemical, paper & pulp, paint & varnish, ceramics, etc., because of their particle-dispersing capacity. They can be applied either of solid particles and liquid particles. The solid particles may be water-insoluble or sparingly soluble inorganic particles of calcium carbonate, sachine white, talc, red oxide, cement, magnesium hydroxide, zinc white, barium sulfate, kaolin, clay, etc. or waterinsoluble or sparingly soluble organic particles of cocoa powder, fruit pulp, solid matters of miso (bean paste), solid matters of soup, powdery agricultural chemicals (for example, zinc ethylenbis(dithiocarbamate), bis(dimethylthiocarbamoyl)disulfide, tetrachloroisophthalonitrile, N-(trichloromethylthio)-4-cyclo-hexene-1,2-dicarboximide, N-(1,1,2,2,-tetrachloroethylthio)-4-cyclohexene-1,2-dicarboximide, m-tolylmethylcarbamate, 3',4'-dichloropropionanilide, 2-chloro-4,6-bis(ethylamino)-1,3,5-triazine, methyl-3,4-dichlorocarbanilate, methylene bisthiocyamate), pharamaceutical medicines, etc. On the other hand, the liquid particles may be liquid agricultural chemicals (for example, S-1,2-bis(ethoxycarbonyl)ethyl dimethyl phosphorothiolothionate, diethyl 2-isopropyl-4-methyl-6-pyrimidinyl phosphorothionate, etc.) or pharmaceutical medicines.

As to the particle-dispersing capacity of the partial degradation products, further detailed explanation is given hereinafter.

For example, it is possible by addition of a small amount of them, to reduce the viscosity of a calcium carbonate slurry containing 50% (by weight) of calcium carbonate and the viscosity of kaolin slurry containing 60% (by weight) of kaolin, each to 6000 cps or less.

Further, it is possible, by addition of them to powdery food stuffs such as cocoa, instant miso soup, instant soup, instant zenzai (thick red bean-meal soup with sugar), instant shiruko (red-bean soup with sugar), etc., to accelerate dispersion of the contents of the powdery food stuffs into water and prevent sedimentation of suspended particles (solid matters) for a long time.

As for agricultural chemicals, they prevent aggregation/separation of the active ingredient particles in flowable preparations, emulsion preparations and aqueous solution preparations for a long time, as they are used on preparing these preparations, and accelerate dispersion of the active ingredient particles and the carrier into water and prevent sedimentation of the particles for a long time, as the preparations mentioned above or wettable preparations containing them are diluted with water.

(iii) They are useful as a quality-improving agent for various food stuffs, because they have a complexforming capacity with protein and starch, in addition to the surface-activate capacity and the particle-dispersing capacity.

① They are useful as a quality-improving agent for starchy food stuffs.

For example, they have quality-improving effects such as the so-called aging-preventing effect which prevents or suppresses the hardening of bread and noodles due to the degeneration of starch; a water-holding property-improving effect which prevents or retards the hardening of bread and noodles due to drying; a dough-regulating effect which regulates fineness and stickiness of the dough suitably on making bread and noodles, promotes the rising of dough due to the fermentation with yeast on making bread and, as a result, provides bread having fine and uniform cellular texture; and the like.

On making bread, they are suitably added to the material in an amount of 0.01-5% (by weight) of wheat flour. By such addition, the dough becomes smooth and is improved in its water-holding property and its aging is prevented or suppressed. Moreover, the cellular texture of the bread obtained becomes fine and uniform, and the volume of the bread obtained is much increased compared with the cases using conventional quality-improving agents. When they are used in an amount less than 0.01% (by weight), the quality-improving effect is not revealed well. On the other hand, addition in an amount more than 5% (by weight) is also not preferable, any effect compensating the economical demerit being not brought about. Usually, it is preferred to use them in an amount of 0.05-3% (by weight), particularly 0.1-1% (by weight), in view of the total quality-improving effect and the cost. However, when the main purpose of using them resides in the regulation of dough and the increase in the volume of bread, an amount of some 0.02-1.0% (by weight) is sufficient. On the other hand, when the main purpose resides in the improvement in proventing the aging of bread, it is preferred to use them in an amount of 0.05% (by weight) or more.

On making noodles, they are suitably added to the material in an amount of 0.01-5% (by weight), preferably 0.05-3% (by weight), of wheat, buckwheat, rice rye, rye, maize, or the like.

By the addition of them, it is possible to prevent or suppress the aging of noodles, to improve the palatal impression and the loosening of noodles, and also to improve the yield of noodles on making and the preservability of the resulting noodles. Further, it is possible by addition of them to accelerate the restoration of dried noodles and instant noodles, and also to prevent adhesion to the packing material of packed, boiled noodles.

② They are useful as a quality-improving agent for proteinic food stuffs (containing protein as the main component in an amount of 40% (by weight) of the total solid matters).

For example, on preparing animal proteinic food stuffs containing fish or meat as the main material, such as boiled fish paste or ham, sausage, hamburger, fried ball of mincemeat, etc., it is possible by using a suitable amount of them to obtain those protienic food stuffs which have an improved shaping property, a good shape-keeping property and texture and an improved palatal impression. Further, it is also possible because of such qualityimproving effect to increase the amount of vegetable protein incorporated into the animal proteinic food stuffs, which has been hitherto limited to at the most 10% (by weight) or so, because of its dispersibility. Furthermore, they reveal a quality-improving effect also on vegetable proteinic food stuffs such as soya bean proteinic food stuffs, bean-curds, etc. by adding them to the vegetable proteinic food stuffs on the preparation thereof. By the addition of them, the stability, the shape-keeping property and the texture of soya bean proteinic food stuffs are improved and the elasticity of soya bean-curds is enhanced. The amount of addition in these cases is suitably 0.05-10% (by weight), preferably 0.5-5% (by weight), of the material of the proteinic food stuffs. With an amount less than 0.5% (by weight), the above-mentioned various quality-improving effects are not revealed sufficiently and, with an amount more than 10% (by weight), the quality-improving effects attained do not correspond to the cost increased.

③ They are useful as a quality-improving agent for creamy processed milk product.

The creamy processed milk products here include, besides the representative ones such as the above-mentioned coffee whitener, whip cream, ice cream, etc., those liquid foamy food stuffs which contain at least solid matters of milk, oils and fats, and water as their indispensable components.

For example, although a raw cream obtained from milk or a processed milk product containing solid matters of milk, skim milk, etc., oils and fats, and water as its main components, is used, by itself, as coffee whitener and, by making it to hold air by agitation, as whip cream; by addition of the partial degradation products of the present invention to the former, a coffee whitener which is suppressed in the feathering phenomenon and the generation of surface fatty film can be provided in convenience and, by addition to the latter, a foamy product (whip) which is stabilized and has a good shape-keeping property can be provided in convenience. Further, the partial degradation products reveal also various quality-improving effects on ice cream, such as stabilization of the shapekeeping property, etc.

The amount of addition here is suitably 0.02-5% (by weight), preferably 0.1-2% (by weight), per the materials (total solid matters) of the processed milk product. Addition of an amount less than 0.02 (by weight) gives insufficient quality-improving effect, and addition of an amount more than 5% (by weight) does not bring about any merit of effect which corresponds to the elevated cost.

④ They are useful as a quality-improving agent for emulsified oily food stuffs.

The emulsified oily food stuffs here include, besides the representative ones such as margarine, shortening, dressing, etc., those various oily food stuffs in which the oily phase and the aqueous phase are kept at least at a state of emulsion.

For example, in solid-type emulsified oily food stuffs, they reveal a quality-improving effect such as an effect of making the constitution of oily phase and aqueous phase fine and simultaneously suppressing the separation of the two phases which may occur on dissolution, and the like. In fluid or semifluid emulsified oily food stuffs such as dressings, etc., they reveal an effect of keeping the stabilized emulsion state for a prolonged time. Further, the stabilizers according to the present invention give an effect of suppressing the separation of oily phase and aqueous phase which may occur on preparing emulsified oily food stuffs and the various damages resulting from such separation.

The amount of addition is suitably 0.01-5% (by weight), preferably 0.03-2% (by weight), per the total amount of the emulsified oily food stuffs, in view of the effect of stabilizing the emulsion and the effect of making the dispersed phase fine. Addition of an amount less than 0.01% (by weight) does not reveal the above effect sufficiently, and addition of an amount more than 5% (by weight) is economically unsuitable, not bringing about any effect corresponding to the increased amount.

Each of the effects ①-④ as described above is superior to that attained by coventionally used surface active agents or usual grain protein partial degradation products.

Although the protein partial degradation products of the present invention can be used as a surface active agent, a dispersing agent, or a quality-improving agent for various food stuffs, in the form of their aqueous solution obtained by the degradation treatment, it is also possible to use them in the form of powder which is obtained by drying and pulverizing the aqueous solution. It is also suitable to use their purified products obtained by desalting treatment such as ultra-filtration, etc., or decloring treatment.

Among the protein partial degradation products of the present invention, those having an average molecular weight of 17000-70000 have a surface-activating capacity higher than the sucrose/fatty acid esters and accordingly are especially useful as a surface active agent, and those having an average molecular weight of 700-70,000 have a high particle-dispersing capacity and a high quality-improving capacity for food stuffs and are especially useful as a particle-dispersing agent or a quality-improving agent for food stuffs.

The partial degradation products of the present invention may be used in combination with other known surface active agents, in accordance with the purpose of use. As such known surface active agents, relatively oleophilic surface active agents, i.e., polyhydric alcohol/fatty acid esters, such as monoglycerides, sorbitan esters, glycol ethers, sucrose/fatty acid esters, etc. and lecithin, and the like are sued. Among these known surface active agents, moncglycerides and sucrose/fatty acid esters give various synergetic effects when used in combination with the partial degradation products of the present invention in a ratio (by weight) of 1:6-6:1, preferably 1:4-4:1.

Further, the partial degradation products of the present invention may be used also in combination with the conventional preservatives such as ethanol, propionic acid, lactic acid, sorbic acid, dehydroacetic acid, sodium chloride, etc.

On using them as a particle-dispersing agent, other dispersing agents, for example, polysaccharides such as gum arabic, pectin, CMC, gum xanthenic, alginic acid, etc, synthetic high molecular compounds such as polyacrylic acid, polyvinyl alcohol, etc., and the like, may also be used in combination.

EXAMPLE

The present invention is explained in detail by following Examples and Tests.

Examples 1 to 12 (Preparation of partial degradation products of wheat gluten treated with acid, followed with alkali)

Twenty grams of wheat gluten (a reagent grade from Wako Pure Chemicals Ltd., JAPAN) were added to each of flasks containing 100 g of hydrochloric acid equivalent to 0.5 g, 1 g, 2 g or 4 g of hydrogen chloride. Each of the mixtures was heated at 80° C. or 100° C. for 60 minutes under stirring, neutralized by sodium hydroxide and diluted with pure water into a total weight of 200 g. Thus, four kinds of 10% aqueous solutions of wheat glutens partially degradated by the acid which are shown in Table 1 were obtained. One hundred grams of each of the above solutions were put in a flask to which sodium hydroxide or sodium carbonate in the range of 0.5 g to 2 g was added. The mixture was heated at a temperature of 80° C. to 150° C. for a period of 30 minutes to 360 minutes, neutralized by hydrochloric acid and diluted with pure water into a total weight of 200 g. Thus, Test samples 1 to 12 of partial degradation products of the present invention were obtained.

Conditions for partial degradation and average molecular weights of the degradation products are shown in Table 1.

Test sample 1 desalted by precipitation at isoelectric point or dialysis was almost odorless and tasteless.

Examples 13 to 16 (Preparation of partial products of maize gluten and soya bean gluten by treatment with acid followed by alkali)

Maize gluten (from Nihon Shokuhin Kako Co., Ltd., JAPAN) as the starting material was put into the same partial degradation treatments with acid and alkali as those employed in Examples 6 and 1, whereby Test samples 13 and 14 having a weight average molecular weight of 11,800 and 27,100, respectively were obtained.

Using a soya bean protein prepared by defatting a commercially available dried soya bean curd (yu ba) with acetone, as a starting material, the partial degradation treatments with acid and alkali were performed under the same conditions as those employed in Examples 6 and 1, whereby Test samples 15 and 16 having a weight average molecular weight of 12,000 and 29,000, respectively were obtained.

Examples 17 and 18 (Preparation of partial degradation products of wheat gluten by treatment with alkali, followed with acid)

TABLE 1

| Test sample No. | Addition of hydrogen chloride (g) | Temperature (°C.) | Time (minute) | Addition of sodium hydroxide (g) | Temperature (°C.) | Time (minute) | Average molecular weight |
|---|---|---|---|---|---|---|---|
| 1 | 1 | 100 | 60 | 0.5 | 100 | 60 | 48000 |
| 2 | " | " | " | 1 | " | " | 41000 |
| 3 | " | " | " | 2 | " | " | 16500 |
| 4 | " | " | " | 2 | 150 | 360 | 980 |
| 5 | 2 | 100 | 60 | 0.5 | 100 | 60 | 42200 |
| 6 | " | " | " | 1 | " | " | 22000 |
| 7 | " | " | " | 2 | " | " | 15000 |
| 8 | " | " | " | " | 150 | 360 | 870 |
| 9 | 4 | 100 | 60 | 1 | 100 | 60 | 18000 |
| 10 | " | " | " | 2 | 150 | 360 | 670 |
| 11 | 2 | 100 | 60 | Addition of sodium carbonate (g) 1 | 100 | 60 | 42200 |
| 12 | 0.5 | 80 | 60 | 0.5 | 80 | 30 | 79000 |

Twenty grams of the same wheat gluten as used in Examples 1 to 12 were added to 100 g of an aqueous solution containing 2 g or 4 g of sodium hydroxide. Each of the mixture was heated at 100° C. for 60 minutes with stirring, neutralized by hydrochloric acid and diluted with pure water into a total weight of 200 g. Thus, 10% aqueous solutions of wheat gluten partially degradated by the alkali were obtained. To 100 g of each of the above solutions was added hydrochloric acid equivalent to 0.5 g or 1 g of hydrogen chloride and the resultant was heated at 100° C. for 60 minutes with stirring, neutralized by sodium hydroxide and diluted with pure water into a total weight of 200 g. Thus, Test samples 17 and 18 shown in Table 2 were obtained.

Conditions for partial degradation and average molecular weights of the degradation products are shown in Table 2.

TABLE 2

| | Degradation by alkali | | | Degradation by acid | | | |
|---|---|---|---|---|---|---|---|
| Test sample | Addition of sodium hydroxide (g) | Temperature (°C.) | Time (minute) | Addition of hydrochloric acid (g) | Temperature (°C.) | Time (minute) | Average molecular weight |
| 17 | 2 | 100 | 60 | 0.5 | 100 | 60 | 38200 |
| 18 | 4 | 100 | 60 | 1 | 100 | 60 | 13200 |

Examples 19 and 20 (Preparation of partial degradation products of wheat qluten treated with enzyme, followed with alkali)

Twenty grams of the same wheat gluten as used in Examples 1 to 12 were added to a flask containing 150g of 0.1 N hydrochloric acid to obtain an aqueous solution of pH 1.5. The solution was treated with 2.2 g of pepsin and warmed at 37° C. for 90 minutes under stirring. The resultant was neutralized by sodium hydroxide and diluted with pure water into a total weight of 200 g to obtain a 10% aqueous solution of wheat gluten partially degradated by the enzyme. To two flasks containing 100 g of the above solution were added 1 g and 2 g of sodium hydroxide, respectively. The mixtures were heated at 100° C. for 60 minutes under stirring, neutralized by hydrochloric acid and diluted with pure water into a total weight of 200 g, by which Test samples 19 and 20 were obtained. Test samples 19 and 20 show average molecular weight of 29,000 and 14,000, respectively.

Example 21 (Preparation of partial degradation product of wheat gluten treated with reducing agent, followed by alkali)

Twenty grams of the same wheat gluten as used in Examples 1 to 12 were added to 100 g of an aqueous solution containing 4 g of sodium sulfite. The mixture was heated at 30° C. for 60 minutes under stirring and diluted with pure water into a total weight of 200 g to obtain 10% aqueous solution of wheat gluten partially degradated by the reducing agent. To 100 g of the above solution was added 1 g of sodium hydroxide and the mixture was heated at 100° C. for 60 minutes under stirring, neutralized by hydrochloric acid and diluted with pure water into a total weight of 200 g, by which Test sample 21 having average molecular weight of 39,500 was obtained.

Example 22 (Preparation of partial degradation product of wheat gluten treated with alkali and enzyme in reverse order of Example 19)

Twenty grams of the same wheat gluten as used in Examples 1 to 12 were added to 100 g of an aqueous solution containing 2 g of sodium hydroxide. The mixture was heated at 100° C. for 60 minutes under stirring, neutralized by hydrochloric acid and diluted with pure water into a total weight of 200 g, by which 10% aqueous solution of wheat gluten partially degradated by alkali was obtained. To 100 g of the above aqueous solution was added a reagent of hydrochloric acid to obtain an aqueous solution of pH 1.5. The resultant was treated with 0.1 g of pepsin and heated at 37° C. for 90 minutes. The mixture was neutralized by sodium hydroxide and diluted with pure water into a total weight of 200 g, by which Test sample 22 having an average molecular weight of 24,500 was obtained.

Example 23 (Preparation of partial degradation product of wheat gluten treated with alkali and oxidizing agent)

Twenty grams of the same wheat gluten as used in Examples 1 to 12 were added to 100 g of an aqueous solution containing 2 g of sodium hydroxide. The mixture was heated at 100° C. for 60 minutes under stirring, neutralized by hydrochloric acid and diluted with pure water into a total weight of 200 g, by which 10% aqueous solution of wheat gluten partially degradated by the alkali was obtained. To 100 g of the above solution was added hydrogen peroxide equivalent to 0.5 g of $H_2O_2$. The mixture was heated at 40° C. for 60 minutes under stirring, to which sodium thiosulfate equivalent to the remaining $H_2O_2$ was added. The resultant was diluted with pure water into a total weight of 200 g, by which Test sample 23 having an average molecular weight of 37,000 was obtained.

The various properties of the partially degradated proteins of the present invention obtained in Examples 1 to 23 are shown in Table 3.

point that the pH curve becomes a gentle slope is taken as the isoelectric point.

Buffering action

Figure 1B:
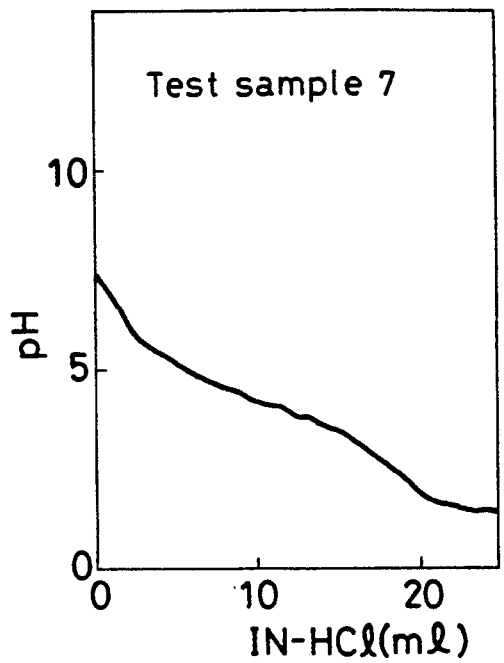
Figure 1C:
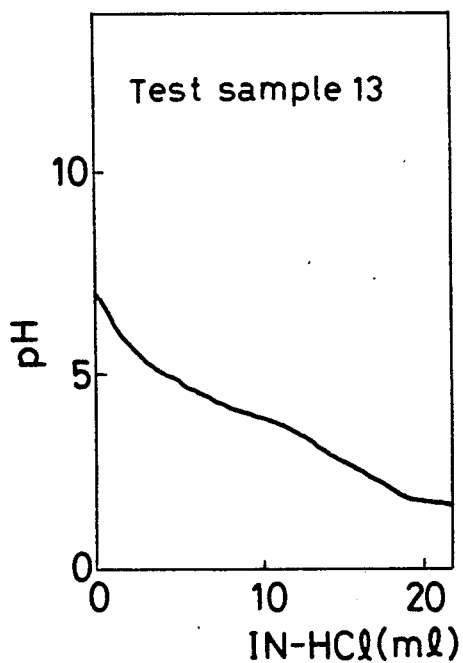
Figure 1D:
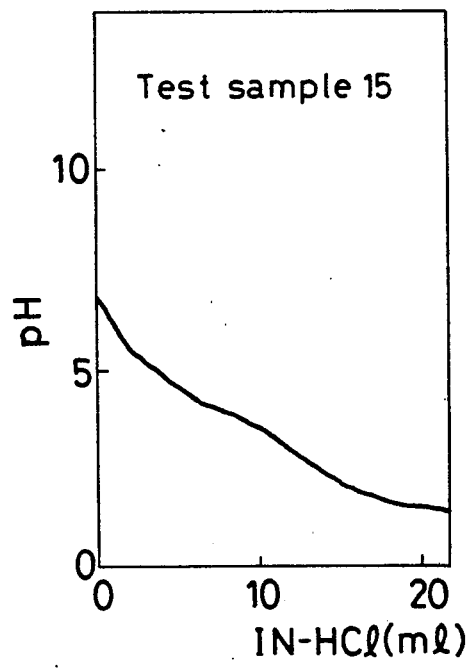

The amount of 1N-HCl required to lower the pH from 6 to 2 on the curve obtained in the measurement of the isoelectric point is taken as the value of the buffering action. The curves for Test samples 1, 7, 13 and 15 are shown in FIGS. 1a, 1b, 1c and 1d.

UV, absorption

UV absorbance is measured in the range of 800–200 nm by use of the Hitachi U-3200 type spectrophotometer.

IR absorption

IR absorbance is measured by the KBr method using the Hitachi 216-10 type IR spectrophotometer.

Amido type nitrogen and amino type nitrogen

Pretreatment

TABLE 3

| | Test sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Material | W | W | W | W | W | W | W | W | W | W | W | W |
| Average molecular weight | 48000 | 41000 | 16500 | 980 | 42200 | 22000 | 15000 | 870 | 18000 | 670 | 42200 | 79000 |
| Isoelectric point | 4.6 | 4.5 | 4.4 | 4.1 | 4.5 | 4.3 | 4.4 | 4.0 | 4.0 | 4.1 | 4.3 | 4.8 |
| Buffering [1N-HCl(ml)/5 g] action | 10 | 16 | 17 | 22 | 17 | 13 | 18 | 20 | 20 | 22 | 16 | 3 |
| Xanthoproteic reaction | + | + | + | + | + | + | + | + | + | + | + | + |
| Ninhydrin reaction | + | + | + | + | + | + | + | + | + | + | + | + |
| UVλmax. (nm) | 274.0 | 275.2 | 273.6 | 275.1 | 272.8 | 272.4 | 271.6 | 273.7 | 273.0 | 272.8 | 271.8 | 273.2 |
| IR absorption (cm$^{-1}$) | 3400 | | | | | 3400 | 3400 | | | 3400 | | |
| | 1630 | | | | | 1630 | 1630 | | | 1630 | | |
| | 1400 | | | | | 1400 | 1400 | | | 1400 | | |
| Amide type nitrogen (%) | 1.63 | | 0.26 | 0.07 | | 0.57 | 0.18 | | | 0.06 | | 2.52 |
| Amino type nitrogen (%) | 0.39 | | 0.48 | 0.53 | | 0.43 | 0.51 | | | 0.54 | | 0.35 |

| | Test sample No. | | | | | | | | | | |
|---|---|---|---|---|---|---|---|---|---|---|---|
| | 13 | 14 | 15 | 16 | 17 | 18 | 19 | 20 | 21 | 22 | 23 |
| Material | C | C | B | B | W | W | W | W | W | W | W |
| Average molecular weight | 11800 | 27100 | 12000 | 29000 | 38200 | 13200 | 29000 | 14000 | 39500 | 24500 | 37000 |
| Isoelectric point | 4.2 | 4.4 | 4.2 | 4.3 | 4.5 | 4.3 | 4.2 | 4.1 | 4.3 | 4.2 | 4.3 |
| Buffering [1N-HCl(ml)/5 g] action | 17 | 8 | 15 | 8 | 16 | 19 | | 18 | | | |
| Xanthoproteic reaction | + | + | + | + | + | + | + | + | + | + | + |
| Ninhydrin reaction | + | + | + | + | + | + | + | + | + | + | + |
| UVλmax. (nm) | 274.0 | 273.5 | 266.8 | 269.1 | 273.0 | 275.2 | 271.4 | 272.6 | 273.5 | 273.8 | 274.0 |
| IR absorption (cm$^{-1}$) | 3400 | | 3400 | | | | 3400 | | 3400 | | |
| | 1630 | | 1630 | | | | 1630 | | 1630 | | |
| | 1400 | | 1400 | | | | 1400 | | 1400 | | |
| Amide type nitrogen (%) | 1.37 | | | 0.94 | | 0.81 | 2.95 | | 0.91 | | 1.18 |
| Amino type nitrogen (%) | 0.39 | | | 0.48 | | 0.45 | 0.56 | | 0.62 | | |

The symbols of W, C and B used in Table 3 mean wheat gluten, maize gluten and soya bean protein, respectively and the blank in Table 3 means "not measured" or "not tested".

The methods of measurement of various properties are as follows.

Average molecular weight

The value is determined by Gel Filtration Method using sodium polystyrenesulfonates having molecular weight of 1,600, 6,500, 16,000, 65,000 or 88,000 as standard substances, and Sephadex G-75 or G-100 (available from Pharmacia Ltd.) as the carrier.

Isoelectric point

One hundred grams of each of Test samples 1 to 23 are put in a beaker, to which each 1 ml portions of 1N-HCl is added at room temperature under stirring, while pH value is measured. The value of pH at the The test sample is concentrated in vacuo under an alkaline condition to remove ammonia before the following measurements.

Amide type nitrogen

A portion of the sample is subjected to thermal decomposition in a hydrochloric acid solution. The resultant is adjusted with sodium hydroxide to pH 10 and distilled. The value is obtained by measuring the distillate using the spectrophotometry (JIS K0102 Indophenol method).

Amino type nitrogen

1N-HCl is gradually added to a portion of the sample to obtain a pH-HCl curve. From the curve, the amount (a ml) of 1N-HCl required to lower the pH from 11 to 5 is obtained.

On the other hand, 1N-HCl is added to the other same amount of the sample into pH 6.8 and then 37% formaldehyde solution is added (about 2.5 times as much as the amount of the sample). The resulting solution is made its pH to more than 11 by addition of 1N-NaOH and then 1N-HCl is added to obtain a pH-HCl curve, from which the amount (b ml) of 1N-HCl required to lower the pH from 11 to 5 is obtained (Formol Titration Method). Further 37% formalin solution in the same amount as used above is titrated with 1N-HCl in the same manner as in the above titration to obtain a pH-HCl curve, from which the amount (c ml) of 1N-HCl required to lower the pH from 11 to 5 is obtained.

The amount of amino type nitrogen is obtained from the value of a-(b-c) ml. Each of the measurements is expressed as % by weight with respect to the sample.

Comparative examples 1 to 3 (Preparation of partial degradation products of wheat gluten by acid)

Twenty grams of wheat gluten (a reagent grade from Wako Pure Chemicals Ltd., JAPAN) were added to each of three flasks containing 100g of hydrochloric acid containing 1 g, 2 g and 4 g of hydrogen chloride. Each of mixtures was heated at 100° C. for 60 minutes under stirring, neutralized by sodium hydroxide and diluted with pure water into a total weight of 200 g to obtain Comparative test samples 1 to 3 containing a partial degradation product.

Conditions for the degradation and weight average molecular weights of the degradation products are shown in Table 4.

TABLE 4

| Comparative test sample No. | Addition of hydrochloric acid (g) | Temperature (°C.) | Time (min.) | Average molecular weight |
|---|---|---|---|---|
| 1 | 1 | 100 | 60 | 91,000 |
| 2 | 2 | " | " | 64,000 |
| 3 | 4 | " | " | 47,000 |

Comparative example 4 (Preparation of partial degradation product of wheat gluten by enzyme)

Twenty grams of the same wheat gluten as used in Comparative example 1 were added to a flask containing 150 g of 1 N hydrochloric acid to obtain an aqueous solution of pH 1.5. The gluten in the solution was treated with 0.2 g of pepsin and warmed at 37° C. for 90 minutes under stirring. The resultant was neutralized by sodium hydroxide and diluted with pure water into a total weight of 200 g to obtain Comparative test sample 4 having an average molecular weight of 60,000.

Comparative example 5 (Preparation of partial degradation product of wheat gluten by reducing agent)

Twenty grams of the same wheat gluten as used in Comparative example 1 were added to 100 g of an aqueous solution containing 4 g of sodium sulfite. The mixture was heated at 30° C. for 60 minutes under stirring and diluted with pure water into a total weight of 200 g to obtain Comparative test sample 5 having an average molecular weight of 79,000.

Comparative examples 6 to 9 (Preparation of partial degradation product of wheat gluten by alkali)

Twenty grams of the same wheat gluten as used in Comparative example 1 were added to each of four flasks containing 100 g of a solution containing sodium hydroxide in the range of 0.2 g to 4 g. The mixtures were thoroughly mixed and were heated at a temperature of 80° C. to 100° C. for a period of 30 minutes to 60 minutes under stirring. The resultants were neutralized by hydrochloric acid and diluted with pure water into a total weight of 200 g to obtain Comparative test samples 6 to 9.

Conditions for degradation and average molecular weights of the degradation products are shown in Table 5.

TABLE 5

| Comparative test sample No. | Addition of sodium hydroxide (g) | Temperature (°C.) | Time (min.) | Average molecular weight |
|---|---|---|---|---|
| 6 | 2 | 100 | 60 | 47,000 |
| 7 | 4 | " | " | 20,200 |
| 8 | 0.5 | 80 | 30 | 80,500 |
| 9 | 0.2 | " | " | 101,000 |

The following tests were carried out on Test samples of the present invention and Comparative test samples.

Test 1 (Determination of surface tension)

Of Test samples and Comparative test samples prepared in Examples and Comparative examples, respectively, a sucrose fatty acid ester (Comparative test sample 10) and soya bean lecithin (Comparative test sample 11), the values of surface tension are determined with du Noüy's tensiometer using pure water (solvent) at 25° C. The results are shown in Table 6. The used sucrose fatty acid ester is of the trade name, DK ester F-160 (HLB:15) from DAI-ICHI KOGYO SEIYAKL CO., Ltd., JAPAN and the used soya bean lecithin is of the trade name, Honen lecithin AY from Honen Seiyu Co., Ltd., JAPAN.

Test 2 (Determination of emulsified state maintaining time)

Of Test samples and Comparative test samples prepared in Examples and Comparative examples, a sucrose fatty acid ester and soya bean lecithin, the emulsified state maintaining time is determined by the following method. The results are shown in Table 6.

Test method

The reagent and city water are put into a beaker into a total weight of 70 g so that the mixture is adjusted to pH 7.0 and 30 g of soya bean oil (a reagent from Kishida Kagaku Co., Ltd., JAPAN) are added. The resultant is mixed for 5 minutes by a homomixer at 8000 rpm. Immediately after mixing the emulsion is transferred into a color comparison tube and left a room temperature. Time required until separation of the emulsion begines is defined as an emulsified state maintaining time. The concentration of a partial degradation product of the present invention is 1.0% by weight with respect to the total weight.

Explanation of the results

From the results, it is clear that the partial degradation products of the present invention are excellent in surface tension lowering property and emulsifying property, and particularly, many products of the present invention are more excellent in any of the various points in comparison with conventional sucrose fatty acid esters. And it is noted that Comparative test samples 6 to 8 are excellent in surface tension lowering property, but are poor in emulsifying property.

Additional tests of emulsifying property of Test samples 1, 5 and 6 using a smaller amount of the sample (concentration:0.3% by weight) gave the value of emulsifying property which is greater than 24 hours. On the other hand, an additional test of the above property of the sucrose fatty acid ester in concentration of 0.3% and 0.15% by weight gave 30 minutes and less than 10 minutes of emulsion state maintaining time, respectively.

Test 3 (Foaming test)

The values of foaming property of Test samples and Comparative test samples prepared in Examples and Comparative examples, and a sucrose fatty acid ester (Comparative test sample 10) are determined by Ross-miles test (JIS K-3362) in concentration of 0.3% using pure water as a solvent at 25° C. The results are shown in Table 6.

Test 4

It is known that surface active agents give an influence on the behavior of viscosity of starch suspension. An influence of the products of the present invention and other conventional surfactants upon gelatinization of starch is tested by the following method.

One gram of Test sample of the present invention and 20 g of potato starch (a reagent) were dispersed and dissolved in city water at 50° C. and the solution was diluted with city water at 50° C. into 500 ml. The viscograph from BRABENDER Co., Ltd., was operated at 77 rpm using the above solution as a sample under the following temperature changing condition. The temperature of the sample was raised from 50° C. to 95° C. at the rate of 1.5° C./min., and was maintained at 95° C. for 45 mintues. Then, the temperature was lowered to

TABLE 6

| | Surface tension (dyne/cm) | | Emulsified state maintaining time (min or hour) | Foaming property (mm) | |
|---|---|---|---|---|---|
| | Addition of 0.1% of the sample | Addition of 0.3% of the sample | | Immediately after foaming | 5 minutes after foaming |
| Comparative test sample | | | | | |
| 1 | 59.7 | 58.0 | <10 (mins) | | |
| 2 | 61.0 | 57.2 | <10 (mins) | 8 | 6 |
| 3 | 55.0 | 52.9 | <10 (mins) | 10 | 4 |
| 4 | 60.9 | 56.8 | <10 (mins) | | |
| 5 | 67.5 | 61.5 | <10 (mins) | 15 | 7 |
| 6 | 32.5 | 31.0 | <10 (mins) | | |
| 7 | 32.0 | 30.8 | <10 (mins) | | |
| 8 | 48.7 | 46.0 | <10 (mins) | | |
| 9 | 60.9 | 60.1 | <10 (mins) | | |
| 10 | 34.5 | 34.2 | 8 hrs | 34 | 31 |
| 11 | 63.5 | 62.7 | <10 (mins) | | |
| Test sample | | | | | |
| 1 | 34.5 | 31.7 | more than 24 hrs | | |
| 2 | 33.0 | 30.9 | 24 hrs | | |
| 3 | 31.0 | 29.8 | 8 hrs | | |
| 4 | 30.5 | 29.2 | 1 hrs | | |
| 5 | 34.8 | 33.8 | more than 24 hrs | | |
| 6 | 34.7 | 34.3 | " | <1 | <1 |
| 7 | 30.8 | 30.3 | 5 hrs | 1 | <1 |
| 8 | 31.3 | 30.7 | 5 hrs | <1 | <1 |
| 9 | 34.5 | 33.5 | 24 hrs | | |
| 10 | 31.1 | 30.6 | 20 mins | 1 | <1 |
| 11 | 34.7 | 31.9 | more than 24 hrs | | |
| 12 | 48.6 | 45.2 | 40 mins | | |
| 13 | 34.0 | 32.0 | 24 hrs | 1 | <1 |
| 14 | 34.9 | 33.1 | more than 24 hrs | | |
| 15 | 30.9 | 29.7 | 5 hrs | 1 | <1 |
| 16 | 31.3 | 30.1 | more than 24 hrs | | |
| 17 | 32.8 | 30.8 | 24 hrs | 1 | <1 |
| 18 | 31.2 | 30.4 | 5 hrs | | |
| 19 | 33.0 | 32.1 | 8 hrs | <1 | <1 |
| 20 | 32.0 | 30.9 | 5 hrs | | |
| 21 | 34.4 | 33.9 | 12 hrs | | |
| 22 | 33.2 | 32.2 | 8 hrs | | |
| 23 | 34.2 | 32.9 | 10 hrs | | |
| Blank | | 72.7 | <10 (mins) | | |

*The blanks mean "not tested".

Consideration of the Results

Test samples of the present invention are much lower in foaming property in comparison with the other samples. Surface active agents which are lower in foaming property so as to permit to facilitate rinsing have been desired as a detergent for laundering and washing foods or tableware. But surface active agents which fully satisfy the above and have higher safety are not found yet. Test samples of the present invention can be efficiently used for these applications.

50° C. at the rate of 1.5° C./min. During the change of temperature, the viscosity of the solution was recorded. The gelatinization initiating temperature and the highest viscosity of the solution are shown in Table 7.

TABLE 7

| Test sample No. | Gelatinization initiating temperature (°C.) | The highest viscosity (B.U.) |
|---|---|---|
| Not added | 66.0 | 720 |
| 1 | 77.0 | 560 |

TABLE 7-continued

| Test sample No. | Gelatinization initiating temperature (°C.) | The highest viscosity (B.U.) |
|---|---|---|
| 7 | 86.0 | 480 |

Consideration of the results

The products of the present invention were recognized to have a characteristic that they raise up the gelatinization initiating temperature of starch and reduce the viscosity at the time of gelatinization. Accordingly, the products of the present invention can be used as a softener or an aging inhibitor for bread.

Test 5 (Bread baking test)

This test was carried out on the following samples, namely, Test samples and Comparative test samples prepared in Examples and Comparative examples, sucrose fatty acid ester (Comparative test sample 10), palmitic acid monoglyceride of the trade name "Sunsoft" No. 8001 from Taiyo Kagaku Co., Ltd., JAPAN (Comparative test sample 12), wheat gluten of a reagent from Wako Pure Chemical Co., Ltd., JAPAN (Comparative test sample 13), and the partial degradation product obtained by the following method (Comparative test sample 14).

Preparation of Comparative test sample 14

Twenty grams of the same wheat gluten as used in Examples 1 to 23 was added to 100 g of an aqueous solution containing 4 g of sodium sulfite. The mixture was heated at 30° C. for 60 minutes under stirring. Hydrochloric acid was added to obtain an aqueous solution of pH 1.5. The gluten in the solution was treated with 0.2 g of pepsin and warmed at 37° C. for 90 minutes under stirring. The resultant was neutralized by sodium hydroxide and diluted with pure water into a total weight of 200 g, by which Comparative test sample 14 having an average molecular weight of 36,000 was obtained.

A. Baking method

The following raw materials were baked using a bread baking device from Matsushita Electric Industrial Co., Ltd., JAPAN and left at 25° C.

| Bread baking device: | National home bakery SD-BT2 type |
|---|---|
| Material: | |
| Hard flour | 280 g |
| Sucrose | 17 g |
| Skimmed milk | 6 g |
| Common salt | 5 g |
| Butter | 11 g |
| Water | 210 g |
| Dried yeast | 2.7 g |
| Baking time | 300 minutes |

Each of Test samples of the present invention and Comparative test samples was added to the materials by mixing and their concentration shown in Table 8 is expressed as percentage by weight with respect to hard flour used.

B. Test results

Volume, water content, its change with time, softness and degree of retrogradation were observed. The breads used for the products of the present invention showed improvements on qualties which are equivalent or more in comparison with those used for Comparative test samples.

Typical examples of the breads added with the products of the present invention and Comparative test samples are shown in Table 8.

Evaluation items mentioned in Table 8 means:

$$\text{Water content (\%)} = \frac{\text{Weight before drying} - \text{Weight after drying for 20 hrs. at 105° C.}}{\text{Weight before drying}} \times 100$$

Change of water content with time (%) = Water content when baked (%) − Water content after lefted (%)

Softness (g/cm): This is expressed with tensile strength measured using the Rheometer (NRM-2010J.D-CW) from Fudo Kogyo Co., Ltd., JAPAN Degree of retrogradation of starch (%): This is measured by the method using beta-amulase-Pullulanase [see K. Kainuma et al., J. Jap. Soc. Starch Soc. 28, No. 4, pp. 235 to 240 (1981)].

TABLE 8

| Sample | Test No. | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| | no addition | Test sample | | | | | | | | | Comparative test sample | | | | | | |
| | | 1 | 4 | | 6 | | | 13 | 16 | 19 | 17 | 13 | 6 | 4 | 14 | 10 | 12 |
| Concentration (% by weight) | | | | | | | | | | | | | | | | | |
| Evaluation | 0 | 0.5 | 0.05 | 0.3 | 0.5 | 3.0 | | 0.5 | | | | | 0.5 | | | | |
| Evaluation items on test bread and the number of day after baking | | | | | | | | | | | | | | | | | |
| Volume (cm³) | — | 2650 | 2940 | 2840 | 2870 | 3110 | 3140 | 3140 | 3070 | 3120 | 2840 | 2830 | 2680 | 2640 | 2800 | 2700 | 2800 | 2870 |
| Water content (%) | 0 | 47.0 | 47.3 | 47.0 | 47.2 | 47.4 | 47.3 | 47.0 | 47.3 | 47.3 | 47.4 | 47.3 | 47.3 | 47.2 | 47.3 | 47.4 | 47.0 | 47.1 |
| Change of water content with time (%) | 2 | 1.9 | 1.4 | 1.3 | | 1.3 | 1.2 | 1.0 | 1.3 | 1.4 | 1.5 | 1.6 | 1.7 | 1.8 | 1.6 | 1.6 | 1.7 | 1.6 |
| | 3 | 2.8 | 1.7 | 1.6 | 2.2 | | 1.6 | 1.3 | 1.5 | 1.7 | 1.9 | 2.0 | 2.8 | 2.6 | 2.3 | 2.2 | 2.1 | 2.0 |
| | 4 | 3.6 | 2.5 | 2.2 | 3.1 | 2.6 | 2.4 | 1.8 | 2.0 | 2.5 | 2.8 | 2.8 | 3.5 | 3.4 | 3.2 | 3.1 | 3.0 | 2.9 |
| Softness (g/cm) | 0 | 9.5 | 4.9 | 5.2 | 7.0 | 5.0 | 4.8 | 5.1 | 4.9 | 4.7 | 6.2 | 6.4 | 9.7 | 7.7 | 7.2 | 8.7 | 7.0 | 6.5 |
| | 2 | 16.7 | 10.2 | 8.1 | | 9.6 | 8.4 | 8.0 | 7.7 | 9.6 | 11.5 | 12.3 | 17.7 | 15.5 | 16.0 | 15.3 | 14.4 | 12.4 |

TABLE 8-continued

| | | Test No. | | | | | | | | | | | | | | | | |
|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 |
| Sample | | no addi- tion | Test sample | | | | | | | | | Comparative test sample | | | | | | |
| | | | 1 | 4 | | | 6 | | 13 | 16 | 19 | 17 | 13 | 6 | 4 | 14 | 10 | 12 |
| | | | | | | | | | Concentration (% by weight) | | | | | | | | | |
| Evaluation | | 0 | 0.5 | 0.05 | 0.3 | 0.5 | 3.0 | | | 0.5 | | | | | 0.5 | | | |
| | 3 | 19.9 | 14.4 | 10.3 | 18.6 | | 11.2 | 10.0 | 10.1 | 14.2 | 16.4 | 16.7 | 21.5 | 18.8 | 17.8 | 16.8 | 17.1 | 16.7 |
| | 4 | 30.1 | 20.5 | 14.7 | 27.0 | 17.3 | 16.0 | 13.2 | 13.4 | 20.4 | 21.3 | 21.4 | 32.6 | 27.7 | 24.3 | 22.6 | 22.6 | 21.8 |
| Degree of | 0 | 27 | 15 | 17 | 23 | 16 | 12 | 10 | 13 | 14 | 18 | 16 | 27 | 24 | 22 | 19 | 20 | 18 |
| retrogradation | 2 | 51 | 42 | 38 | | | 40 | | 36 | 40 | 43 | 45 | 51 | 49 | 47 | 46 | 48 | 46 |
| of starch (%) | 3 | 60 | 47 | 42 | | | 44 | | 40 | 45 | 48 | 50 | 59 | 57 | 54 | 54 | 57 | 51 |
| | 4 | 62 | 52 | 44 | | | 48 | | 42 | 50 | 54 | 55 | 63 | 60 | 57 | 56 | 61 | 54 |

Further the results of evaluation of the bread baked using Test samples 1 and 13 of the present invention together with the sucrose fatty acid ester or palmitic acid monoglyceride are shown in Table 9.

the ones baked using Comparative test samples. The regrogradation of starch of the former is slower than that of the latter (about 1 or 2 days).

TABLE 9

| | | Test No. | | | |
|---|---|---|---|---|---|
| | | 18 | 19 | 20 | 21 |
| Sample | | Test sample 1 + sucrose fatty acid ester | Test sample ]3 + palmitic acid monoglyceride | Test sample 1 + sucrose fatty acid ester | |
| | | Concentration (% by weight) | | | |
| Evaluation | | 0.25 + 0.25 | | 0.1 + 0.4 | 0.4 + 0.1 |
| Evaluation items on test bread and the number of day after baking | | | | | |
| Volume (cm³) | — | 3340 | 3280 | 3060 | 3210 |
| Water content (%) | 0 | 47.3 | 47.4 | 47.3 | 47.3 |
| Change of | 2 | 1.0 | 0.9 | 1.3 | 1.2 |
| water content | 3 | 1.4 | 1.3 | 1.6 | 1.5 |
| with time (%) | 4 | 2.0 | 1.8 | 2.3 | 2.2 |
| Softness | 0 | 4.6 | 4.5 | 4.8 | 4.6 |
| (g/cm) | 2 | 7.7 | 7.5 | 10.0 | 8.3 |
| | 3 | 12.1 | 10.0 | 13.7 | 12.6 |
| | 4 | 15.0 | 13.3 | 18.5 | 15.4 |
| Degree of | 0 | 14 | 10 | 15 | 14 |
| retrograda- | 2 | 40 | 33 | 43 | 40 |
| tion of | 3 | 44 | 37 | 47 | 45 |
| starch (%) | 4 | 47 | 41 | 50 | 47 |

C. Consideration

Bread volume

As shown in Test 2 to 17 in Table 8, addition of 0.5% by weight of Test samples of the present invention permits the bread volume to increase by 7 to 18%, and the same addition as above of Comparative test samples permits the bread volume to increase only by 0 to 8%. This clearly shows the former is superior in bread volume to the latter.

Further, it can be seen from the results of Test Nos. 18 to 21 that the use of sucrose fatty acid ester or palmitic acid monoglyceride together with Test sample of the present invention permits of more increasing of bread volume.

Water retention and softness

The bread baked using Test samples of the present invention is superior in water retention to the control bread and the bread baked using Comparative test samples because change of water content with time of the former is smaller than that of the latter.

The former is also superior in softness to the latter.

Degree of retrogradation of starch

Such degree of the breads baked using Test samples of the present invention decreases in comparison with Test 6 (Noodle making test)

Generally, noodles tend to slowly lower their qualities, such as texture, palatability or untangling property. Accordingly, Test samples of the present invention were compared with Comparative test samples, which are the same as used in Test 5.

A. Preparation of noodles

Medium flour 100 g, common salt 2 g, water 35 g and a predetermined amount of a test sample were kneaded to obtain noodle dough. A strip of the dough of about 1.2 mm in thickness was made by pressing and spreading it with a rod. The strip was cut with No. 20 angle cutter to obtain long noodles. The long noodles were cut to about 30 cm long and the resultant was boiled in water for about 5 minutes and stored in a refrigerator at about 5° C.

The noodles were dipped in boiled water for about 1 minute without stirring and observed their readiness for untangling. Organoleptic test results are shown in Table 10.

B. Test results

The noodles made using Test samples 1 to 23 were superior in untangling property and palatability to those made using Comparative test samples. The results of the organoleptic test in which 10 panelists participate are shown in Table 10, wherein concentration (%) shows percentage by weight of the samples with respect to wheat flour.

TABLE 10

| | Storage day number | 1 | | 3 | | 5 | |
|---|---|---|---|---|---|---|---|
| Sample | Concentration (%) | Untangling property | Palatability | Untangling property | Palatability | Untangling property | Palatability |
| Test sample 6 | 0.5 | ++ | ○ | ++ | ○ | ± | ○ |
| Test sample 13 | 0.2 | + | ○ | ± | ○ | − | Δ |
| | 0.5 | ++ | ○ | ++ | ○ | + | ○ |
| | 1.0 | ++ | ○ | ++ | ○ | + | ○ |
| Test sample 19 | 0.5 | ++ | ○ | + | ○ | ± | Δ |
| Comparative Test sample 13 | 0.5 | ± | Δ | − | X | − | X |
| Comparative Test sample 6 | 0.5 | + | Δ | ± | Δ | − | X |
| Comparative Test sample 14 | 0.5 | + | Δ | + | Δ | ± | X |

(Evaluation of untangling property)
++ : much better than the control
+ : better than the control
± : slightly better than the control
− : equivalent to the control
(Evaluation of palatability)
○ : much better than the control
Δ : slightly better than the control
X : equivalent to the control Test 7 (Stabilization Test on dressings)

A dressing like food consisting of salad oil, water, sucrose and common salt was prepared.

The effect of the following samples to stabilize the dressing like food was measured, i.e., Test samples of the present invention and Comparative test samples prepared by Comparative examples, sucrose fatty acid ester (Comparative test sample 10), palmitic acid monoglyceride (Comparative test sample 12) and wheat gluten (Comparative test sample 13).

Test, method

To 50 ml of city water containing a predetermined amount of the sample are added 12.5 g of sucrose and 3.5 g of common salt and the mixture is stirred to obtain a solution. Eighty ml of a salad oil are added to the solution and the resultant is stirred and mixed for 5 minutes with a homomixer. Thereafter, 12 ml of vinegar are added and the resultant is stirred and mixed for 1 minute to obtain a dressing like food.

The effect of Test sample to stabilize such dressing like food was evaluated with the time required for separation of the food into a water phase and an oil phase.

Test results are shown in Table 11.

TABLE 11

| Sample | Concentration (% by weight to the total weight) | Evaluation of stabilizing effect |
|---|---|---|
| Example | | |
| Test sample 1 | 0.05 | ○ |
| | 0.1 | ⊙ |
| | 0.5 | ⊙ |
| Test sample 3 | 0.5 | ⊙ |
| Test sample 6 | 0.1 | ○ |
| | 0.5 | ⊙ |
| Test sample 12 | 0.5 | ⊙ |
| Test sample 14 | 0.1 | ○ |
| | 0.5 | ⊙ |
| Test sample 16 | 0.5 | ⊙ |
| Test sample 17 | 0.5 | ⊙ |
| Test sample 19 | 0.5 | ○ |
| Test sample 21 | 0.5 | ○ |
| Comparative example | | |
| Comparative test sample 13 | 0.5 | X X |
| Comparative test sample 6 | 0.5 | X |
| Comparative test sample 3 | 0.5 | X |
| Comparative test sample 4 | 0.5 | Δ |
| Comparative test sample 10 | 0.5 | ○ |
| Comparative test sample 12 | 0.5 | Δ |
| not added | 0 | X X |
| Example | | |
| Test sample 1 + Comparative test sample 10 (sucrose fatty acid ester) | 0.01 + 0.04 | ○ |
| | 0.02 + 0.08 | ⊙ |
| | 0.025 + 0.025 | ⊙ |
| | 0.04 + 0.01 | ○ |
| | 0.08 + 0.02 | ⊙ |

The meanings of the symbols expressing the stabilizing effect in Table 11 are as follows.
⊙ ... Stable for more than 72 hours
○ ... Separating into two phases during 30 minutes to 72 hours
Δ ... Separating into two phases during 30 minutes to 24 hours
X ... Separating into two phases within 30 minutes
X ... Separating immediately Consideration As seen from the data in Table 11, the stabilizing effect of Test samples of the present invention is superior to that of Comparative test samples. The use of Test sample with sucrose fatty acid ester is also useful in improving the stabilizing effect and it shows a synergistic effect.

Test 8 (Test on stabilization of margarine)

A margarine like emulsion of water in oil type was prepared by using soya bean oil, hardened fish oil and hardened palm oil.

The effect of Test samples to stabilize the above emulsion was measured.

Test method

A predetermined amount of a Test sample and 80 g of fatty oil were put into a mixing vessel. The mixture was heated to about 90° C. to form a uniform solution or dispersion. Thus an oil phase was prepared. Sixteen grams of water were added to the oil phase and the resultant was stirred and cooled to obtain a uniform emulsion of water in oil type. The composition of fatty oils are as follows.

| Oil | % by weight |
| --- | --- |
| Soya bean oil | 26 |
| Hardened fish oil (m.p. 30° C.) | 68 |
| Hardened palm oil (m.p. 45° C.) | 6 |
| Total | 100 |

The stabilizing effect to the obtained water in oil type emulsified oil composition was evaluated by storing the composition at 25° C. or 35° C. for five days and observing coarseness and separating state of the oil phase and the water phase of the composition when it melts or intermediately melts.

The samples other than Comparative test samples 10 and 12 were desalted by ultrafiltraion and spray-dried. The obtained powder was used for the test. Comparative test samples 10 and 12 in the form of powder were used as such.

Test results

They are shown in Table 12.

TABLE 12

| Sample | Addition (g) | Coarseness after keeping at 25° C. | Separating state after keeping at 35° C. |
| --- | --- | --- | --- |
| Example | | | |
| Test sample 1 | 0.1 | Slightly coarse | Δ |
|  | 0.3 | Smooth | ⊚ |
|  | 1.0 | " | ⊚ |
|  | 3.0 | " | ⊚ |
| Test sample 3 | 1.0 | " | ⊚ |
| Test sample 5 | 1.0 | " | ⊚ |
| Test sample 12 | 1.0 | " | ⊚ |
| Test sample 13 | 1.0 | " | ⊚ |
| Test sample 16 | 1.0 | " | ⊚ |
| Test sample 17 | 1.0 | " | ⊚ |
| Test sample 19 | 0.3 | Slightly coarse | Δ |
|  | 1.0 | Smooth | ○ |
| Test sample 23 | 1.0 | " | ○ |
| Comparative example | | | |
| Comparative test sample 13 | 1.0 | Containing some particles | X |
| Comparative test sample 6 | 1.0 | Slightly separating and coarse | X |
| Comparative test sample 3 | 1.0 | Coarse | Δ |
| Comparative test sample 4 | 1.0 | Containing a few particles | Δ |
| Comparative test sample 10 | 1.0 | Smooth | Δ |
| Comparative test sample 12 | 1.0 | " | ○ |
| Not added | 0 | Containing some particles | X |
| Example | | | |
| Test sample 1 + Comparative test sample 12 (Palmitic acid monoglyceride) | 0.08 + 0.22 | Smooth | ⊚ |
|  | 0.05 + 0.05 | " | ⊚ |
|  | 0.15 + 0.15 | " | ⊚ |
|  | 0.22 + 0.08 | " | ⊚ |

The meanings of the symbols expressing the separating state in Table 12 are as follows.
⊚: Emulsified uniformly
○: Having slight color shading
Δ: Separating a little
X: Separating completely

Consideration

As seen from the data in Table 12, Test samples of the present invention serve to make finer the water phase and the oil phase of margarine and prevent margarine from separation when it melts. Generally, Test samples are superior in such effect to Comparative test samples. The combination use of the test sample with palmitic acid monoglyceride shows a synergistic effect.

Test 9 (Improving effect on the quality of Kamaboko (a boiled fish paste))

A. Test method and condition

The mixture having the composition mentioned below was ground down to obtain ground fish for kamaboko. This ground fish was divided to some portions and the different Test samples were added to each of the portions. The mixtures were kneaded. After measurement of hardness of the finished ground fish, it was packed into a polyvinylidene chloride tube (width of the folded tube:4.5 cm). The resultant was left for 15 hours at 15° C. and heated to 90° C. for 40 minutes to obtain a kamaboko packed in a tube. The breaking strength and the breaking strain of the obtained kamaboko were measured. The hardness of ground fish relates to its formability, and the breaking strength and the breaking strain of the product represent its texture.

| (Composition of kamaboko) | | |
| --- | --- | --- |
| Frozen ground fish of pollack | 2 Kg | (100 parts of weight) |
| Common salt | 44 g | (2.2 parts of weight) |
| Sucrose | 18 g | (0.9 parts of weight) |
| Sodium glutamate | 10 g | (0.5 parts of weight) |
| Mirin (Japanese flavoring spirit) | 10 g | (0.5 parts of weight) |
| Potato starch | 140 g | (7 parts of weight) |

Hardness of ground fish

Ground fish obtained was packed in a glass vessel of 6 cm in diameter and 5 cm in height to prepare a test sample. When the sample was compressed to the height of 45 mm using the Rheometer (NRM-2010J.D-CW) from Fudo Kogyo Co., Ltd., JAPAN, its stress was measured. The value is defined as hardness of ground fish. (Breaking strength and breaking strain of Kamaboko)

The obtained kamaboko was cut to 3cm in height and pressed using the same Rheometer as used above to measure the breaking strength (stress (g) when breaking) and the breaking strain (mm).

B. Test results

The results are shown in Table 13.

TABLE 13

| Sample | Concentration (wt %) | Hardness (g) | Breaking strength (g) | Breaking strain (mm) |
|---|---|---|---|---|
| Example | | | | |
| Test sample 1 | 1 | 916 | 1704 | 21.1 |
| Test sample 2 | 0.2 | 836 | 1536 | 20.0 |
| | 0.5 | 894 | 1802 | 21.7 |
| | 1 | 923 | 1905 | 22.2 |
| | 4 | 1012 | 2060 | 23.9 |
| Test sample 6 | 1 | 920 | 1920 | 22.6 |
| Test sample 13 | | 892 | 1902 | 22.1 |
| Test sample 16 | | 898 | 1910 | 23.2 |
| Test sample 17 | | 888 | 1904 | 22.0 |
| Test sample 19 | | 859 | 1648 | 20.5 |
| Comparative example | | | | |
| Comparative test sample 13 | 1 | 785 | 1506 | 18.0 |
| Comparative test sample 6 | | 822 | 1564 | 18.4 |
| Comparative test sample 3 | | 830 | 1536 | 18.6 |
| Comparative test sample 4 | | 818 | 1524 | 18.5 |
| Comparative test sample 10 | | 834 | 1572 | 18.8 |
| Comparative test sample 12 | | 821 | 1524 | 18.5 |
| Not added Example | 0 | 807 | 1486 | 18.0 |
| Test sample 2 + Comparative test sample 10 (sucrose fatty acid ester) | 0.8 + 0.2 | 978 | 1935 | 23.0 |
| | 0.5 + 0.5 | 995 | 1988 | 23.6 |
| | 0.2 + 0.8 | 920 | 1897 | 22.1 |
| Test sample 2 + Comparative test sample 12 (palmitic-acid monoglyceride) | 0.8 + 0.2 | 971 | 1925 | 22.7 |
| | 0.5 + 0.5 | 989 | 1976 | 23.2 |
| | 0.2 + 0.8 | 913 | 1892 | 20.6 |

Note:
Comparative test samples used are the same ones as used in Test 7.

As shown in Table 13, rigidness of kamaboko can be remarkably improved by Test samples of the present invention.

Further, the combined use of Test sample of the present invention and sucrose fatty acid ester, palmitic acid monoglyceride or the like shows a synergistic effect in improving the quality of protein foods.

Test 10

This test was conducted in the same manner as in Test 9 by replacing 300 g in 2Kg of the frozen ground fish of pollack, which is one ingredient of the kamaboko used in the Test 9, with 300 g of wheat gluten, and the improving effect of Test samples of the present invention on the quality of the kamaboko was evaluated. The results are shown in Table 14.

TABLE 14

| Sample | Concentration (wt %) | Hardness (g) | Breaking strength (g) | Breaking strain (mm) |
|---|---|---|---|---|
| Comparative example | | | | |
| Not added Example | 1 | 772 | 1562 | 18.3 |
| Test sample 2 | 1 | 853 | 1961 | 22.3 |
| Test sample 6 | 1 | 874 | 1970 | 22.7 |
| Test sample 16 | 1 | 830 | 1912 | 23.0 |

Test 11 (Improving effect on the quality of hamburger)

Each of the test samples of the present invention was added to hamburger materials having the below composition containing wheat gluten.

| | |
|---|---|
| Minced pork | 22.5 parts |
| Common salt | 1.0 parts |
| Minced beef | 22.5 parts |
| Minced fat pork | 10.0 parts |
| Onion | 23.4 parts |
| Bread crumb | 6.4 parts |
| Wheat gluten | 10.0 parts |
| Sodium glutamate | 0.3 parts |
| White pepper | 0.1 parts |
| Nutmeg | 0.2 parts |
| Water | 4.0 parts |

TABLE 15

| Sample | Addition (part) | Compatibility | Texture | Flavor |
|---|---|---|---|---|
| Comparative example | | | | |
| Not added Example | 0 | Bad | Bad | Inferior |
| Test example 6 | 1 | Good | Good | Equivalent |
| Test example 13 | 1 | Good | Good | Equivalent |
| Test example 17 | 1 | Good | Good | Equivalent |

This test was conducted employing ten panelists and the results were summarized in Table 15.

The texture and the flavor were evaluated in comparison with the standard hamburger prepared using the same material as mentioned above without wheat gluten.

From the above results, test samples of the present invention improve the palatability and flavor of hamburger.

Test 12 (Improving effect on the quality of soya bean protein material)

Soya bean protein powder (Fujipro R from Fuji Seiyu Co., Ltd., JAPAN) was dissolved in water to obtain a 8% aqueous solution of it. The predetermined amount of each of Test samples of the present invention and Comparative test samples was added to the solution and the mixture was mixed with stirring and spray-dried to obtain a powder product.

The obtained powder was hermetically sealed in a polyethylene tube. It was kept at 25° C. and then the time course of its solubility (NSI:Nitrogen Solubility Index) was determined.

The results are shown in Table 16.

TABLE 16

| Sample | Concentration (wt %) | Solubility (NSI %) Time | | | |
|---|---|---|---|---|---|
| | | 0 | 2 months | 5 months | 10 months |
| Example | | | | | |
| Test sample 2 | 0.2 | 98 | 91 | 80 | 63 |
| | 0.5 | 98 | 94 | 87 | 75 |
| | 1 | 98 | 96 | 90 | 85 |
| | 3 | 99 | 97 | 93 | 88 |
| Test sample 4 | 1 | 98 | 91 | 84 | 73 |
| Test sample 6 | | 98 | 96 | 89 | 84 |
| Test sample 7 | | 98 | 95 | 88 | 83 |
| Test sample 14 | | 99 | 95 | 89 | 82 |
| Test sample 15 | | 98 | 94 | 86 | 80 |
| Test sample 18 | | 98 | 95 | 87 | 82 |
| Test sample 21 | | 99 | 92 | 85 | 77 |
| Test sample 22 | | 99 | 92 | 84 | 74 |
| Test sample 23 | | 98 | 91 | 84 | 73 |
| Comparative example | | | | | |
| Comparative test sample 13 | 1 | 98 | 90 | 76 | 58 |
| Comparative test sample 6 | | 98 | 91 | 79 | 60 |
| Comparative test sample 3 | | 98 | 90 | 78 | 59 |
| Comparative test sample 4 | | 99 | 91 | 78 | 60 |
| Comparative test sample 10 | | 98 | 91 | 83 | 72 |
| Comparative test sample 12 | | 98 | 91 | 81 | 67 |
| Not added | 0 | 98 | 90 | 75 | 57 |
| Example | | | | | |
| Test sample 2 + Comparative test sample 10 | 0.8 + 0.2 | 98 | 97 | 92 | 87 |
| | 0.5 + 0.5 | 99 | 97 | 94 | 91 |
| | 0.2 + 0.8 | 99 | 94 | 88 | 80 |
| Test sample 2 + Comparative test sample 12 | 0.8 + 0.2 | 98 | 96 | 91 | 86 |
| | 0.5 + 0.5 | 98 | 96 | 93 | 89 |
| | 0.2 + 0.8 | 98 | 93 | 87 | 78 |

Note:
Comparative test samples used are the same ones as used in Test 7.

As described above, it was determined that Test samples of the present invention prevented the reduction of solubility of the soya bean protein and stably kept its quality, for example depressing its shrinkage when heated.

Further, it can be seen that the use of Test samples of the present invention, and a combined use of Test sample 2 and sucrose fatty acid ester (Comparative test sample 10) or palmitic acid monoglyceride (Comparative test sample 12) permits more improvement of the above stabilizing effect.

The above soya bean protein or wheat gluten have been used as a bulking agent for meat-balls and hamburgers, and is said also that its addition to foods softens the palatability. But sufficient mixing of the mixture is very difficult when the material is added to minced meat foods, which comes into a problem in the art.

Further, it was confirmed that each of Test samples and 14, and a combination of Test sample 2 and Comparative test sample 10 in the form of powder which are shown in Table 16 could be easily mixed with other materials and also easily homogenized, as a bulking agent. Thus, Test samples of the present invention are very useful as a quality-improving agent for soya bean protein materials.

Test 13 (Improving effect on the quality of tofu (bean curd))

One hundred grams of soya bean were washed with water and water at about 10° C. is added to the soya bean into a total weight of about 250 g, which is left at about 10° C. 15 hours. After addition of 250 g of water, the soya bean was ground, added with Test sample and boiled. After 5 minutes, the height of its foaming was measured, and boiled for 10 minutes. Boiling water was added to make a total weight of 1000 g. The resultant was filtered to separate into soya bean milk and tofu refuse. The tofu milk cooled to 75° C. and it was flocculated by addition of 3 g of calcium sulfate in 30 ml of water at 40° C. After 10 minutes, a tofu product was obtained by pressing.

The height of foaming in above boiling, the yield in weight and the quality (elasticity and solid content) of the obtained tofu are shown in Table 17.

TABLE 17

| Sample | Concentration (wt %) | Height of foam (cm) | Weight of tofu (g) | Elasticity | Solid content (%) |
|---|---|---|---|---|---|
| Example | | | | | |
| Test sample 3 | 1 | 10 | 1780 | Stronger | 11.4 |
| Test sample 7 | 0.2 | 50 | 1540 | " | 12.2 |
| Test sample 7 | 0.5 | 25 | 1670 | " | 11.9 |
| Test sample 7 | 1 | 9 | 1750 | " | 11.6 |
| Test sample 15 | 1 | 18 | 1720 | " | 11.8 |
| Test sample 7 + Comparative test sample 12 | 0.8 + 0.2 | 8 | 1760 | " | 11.6 |
| Test sample 7 + Comparative test sample 12 | 0.5 + 0.5 | 6 | 1780 | " | 11.5 |
| Test sample 7 + Comparative test sample 12 | 0.2 + 0.8 | 15 | 1640 | " | 12.0 |
| Not added | 0 | >100 | 1500 | Ordinary | 12.4 |
| Comparative example | | | | | |
| Comparative test sample 12 | 1 | 20 | 1610 | Slightly Stronger | 12.1 |

Note:
Comparative test sample 12 is the same one as used in Test 7.

It can be seen from the above results that Test samples of the present invention improve the elasticity and the yield in weight of tofu and prevent troublesome foaming, and further such effect is synergistically increased by the combination use of Test sample of the present invention and palmitic acid monoglyceride.

Test 14 (Improving effect on the quality of coffee whitener)

One to three grams of Test sample of the present invention and 30 g of the skimmed milk powder (from Snow Brand Milk Products Co., Ltd., JAPAN) were dispersed or dissolved in hot water at 65° C. to make a total weight of 700 g. The resultant liquid was slowly added with stirring to hardened soya bean oil (raising of melting point, 36° C.) at 70° C. wherein 0.1 g of palmitic acid monoglyceride is dissolved. The mixture was stirred at 70° C. for 10 minutes and homogenized at a pressure of 50 Kg/cm² using a high pressure homogenizer to obtain a coffee whitener.

This coffee whitener was tested by the following method.

Test method

Thirteen grams of roasted Brazilian coffee beans were extracted with 100ml of hot water to 85° C. The obtained coffee liquid was maintained at 80° C. and 10 ml of the above coffee whitener were added. After stirring the grade of feathering (a phenomenon that feather like flocculates of coffee cream or whitener float on the surface of coffee liquid) was determined with the ranks of (+) "feathering occurs", (±) "slight feathering" and (−) "no feathering" and also the time required to form a film of coffee whitener was determined.

Test results

No feathering occurs in the above test of Test samples 1 to 23 of the present invention, and it took more than 10 minutes for all the above samples to form their film. The test results of the typical Test samples together with some Comparative test samples are shown in Table 18.

TABLE 18

| Sample | Addition (g) | Feathering | Time required to form film (minute) |
|---|---|---|---|
| Example | | | |
| Test sample 1 | 3 | (−) | ≧30 |
| Test sample 4 | 3 | (−) | 17 |
| Test sample 6 | 3 | (−) | ≧30 |
| Test sample 7 | 3 | (−) | ≧30 |
| Test sample 7 | 2 | (−) | 22 |
| Test sample 7 | 1 | (±) | 9 |
| Test sample 13 | 3 | (−) | 24 |
| Test sample 16 | 3 | (−) | ≧30 |
| Test sample 18 | 3 | (−) | ≧30 |
| Test sample 19 | 3 | (−) | 16 |
| Test sample 21 | 3 | (−) | 15 |
| Test sample 22 | 3 | (−) | 15 |
| Test sample 23 | 3 | (−) | 11 |
| Not added | 0 | (+) | 2 |
| Comparative example | | | |
| Comparative test sample 13 | 3 | (+) | 2 |
| Comparative test sample 6 | 3 | (+) | 5 |
| Comparative test sample 3 | 3 | (±) | 7 |
| Comparative test sample 4 | 3 | (+) | 3 |
| Comparative test sample 10 | 3 | (±) | 8 |
| Comparative test sample 12 | 3 | (±) | 4 |
| Example | | | |
| Test example 7 + | 1.6 + 0.4 | (−) | ≧30 |
|  | 1 + 1 | (−) | ≧30 |
| Comparative test sample 10 | 0.4 + 1.6 | (−) | 20 |

Note:
Comparative test samples used are the same ones as used in Test 7.

It can be seen from the above results that when the Test sample of the present invention is used in coffee whitener, feathering and film formation are sufficiently prevented and also such effects is synergistically increased by use of a combination of Test sample and Comparative test sample.

Test 15 (Improving effect on the quality of whipping cream)

Forty five parts of hardened soya bean oil (raising of melting point, 36° C.) and Test sample of the present invention or Comparative test sample were added to 65 parts of whole milk, and the mixture was stirred at 70° C. for 15 minutes by use of a homomixer, homogenized at 80 Kg/cm$^2$ using a homogenizer. The emulsified state of the resultant was observed. The emulsion was sterilized by heating at 70° C. for 10 minutes, rapidly cooled to 10° C. and aged at 5° C. for 12 hours in a refrigerator to obtain a cream like oil composition. This composition was stirred at 600 rpm using an electric hand whipper to obtain a whipping cream.

The whipping cream was tested on the following properties.

Evaluation items and test methods (1) Viscosity:Rion BO-2 type viscometer was used.

(2) Overrunning:(Percent increase in maximum foaming volume to initial volume through whipping is calculated by the following formula)

$$\text{Overrunning} = \frac{\text{Weight of the initial composition in a prescribed volume} - \text{Weight of the maximum whipping cream in a prescribed volume}}{\text{Weight of the maximum whipping cream in a prescribed volume}} \times 100$$

(3) Foaming time:The time required for the initial composition to reach to the maximum foaming condition by whipping at 600 rpm using an electric hand whipper.

(4) Duration of the maximum foaming: The time for which the whipping cream can keep its most suitable foaming condition when the cream is whipped in the same manner as in the above (3).

(5) Shape retaining property and surface texture: A . . . good AB . . . slightly better B . . . no good (unpractical)

Test results

The above tests were conducted on Test samples 1 to 23 of the present invention and Comparative test samples. The results of the typical samples are shown in Table 19. The result of the combined use of Test sample 7 and sucrose fatty acid ester (Comparative test sample 10) is also shown in Table 19.

TABLE 19

| Sample | Concentration (% by weight with respect to oil) | Emulsified state | (1) Viscosity (CP) | (2) Overrunning | (3) Foaming time (min/sec.) | (4) Duration of foaming | (5) Shape retaining property | (6) Surface texture |
|---|---|---|---|---|---|---|---|---|
| Example | | | | | | | | |
| Test sample 1 | 1.0 | A | 150 | 120 | 4/10 | 40 sec | A | A |
| Test sample 4 | " | A | 120 | 100 | 5/20 | 40 | A | A |
| Test sample 6 | " | A | 120 | 120 | 5/40 | 45 | A | A |
| Test sample 7 | " | A- | 110 | 130 | 4/20 | 35 | A | A |
| Test sample 7 | 0.5 | AB | 180 | 120 | 3/50 | 25 | A | A |
| Test sample 7 | 0.3 | AB | 350 | 100 | 5/10 | 20 | AB | AB |
| Test sample 14 | 1.0 | A | 140 | 140 | 4/30 | 40 | A | A |
| Test sample 15 | " | A | 120 | 120 | 5/20 | 45 | A | A |

TABLE 19-continued

| Sample | Concentration (% by weight with respect to oil) | Emulsified state | (1) Viscosity (CP) | (2) Over-running | (3) Foaming time (min/sec.) | (4) Duration of foaming | (5) Shape retaining property | (6) Surface texture |
| --- | --- | --- | --- | --- | --- | --- | --- | --- |
| Test sample 17 | " | A | 150 | 130 | 6/40 | 30 | A | A |
| Test sample 19 | " | A | 140 | 135 | 6/10 | 40 | A | A |
| Test sample 21 | " | A | 170 | 120 | 5/50 | 35 | A | A |
| Test sample 23 | " | AB | 220 | 80 | 5/40 | 25 | A | AB |
| Not added Comparative example | 0 | B | — | 55 | 3/20 | 5 | B | B |
| Comparative test sample 13 | 10 | B | 800 | 40 | 7/20 | 5 | B | B |
| Comparative test sample 6 | " | B | 290 | 60 | 7/10 | 5 | B | B |
| Comparative test sample 3 | " | B | 240 | 65 | 6/00 | 15 | B | AB |
| Comparative test sample 10 | " | AB | 150 | 95 | 4/30 | 5 | B | AB |
| Comparative test sample 12 | " | AB | 160 | 150 | 5/20 | 10 | AB | AB |
| Example Test sample 7 + Comparative test sample 10 | 0.4–0.1 0.25–0.25 0.1–0.4 | A A A | 120 110 130 | 130 130 120 | 5/20 5/00 6/10 | 55 70 60 | A A A | A A A |

Note:
Comparative test samples used are the same ones as used in Test 7.

Test 16 (Test of washing for removing dirt which adheres to tablewares or the like, based on JIS K-3370)

1. Test method and condition (i) Preparation of a model of dirty pieces (a) Twenty grams of a mixture of tallow and soya bean oil (1:1), 2.5 g of monoolein and 1 g of Oil Red (Sudan III) were dissolved in 600 ml of chloroform to prepare a bath of stain.

(b) One set of six slide glasses was dipped in the stain bath by the length of about 55 mm of these glasses for 1 to 2 seconds and was slowly taken out of the bath.

(c) The slide glasses to which the stain adheres were air-dried, and subjected to a washing test in a room at a constant temperature and humidity (25° C., 40%RH), according to the following procedure.

(ii) Method of washing test

In a modified Leenerts type detergency tester the six stain adhered slide glasses were settled. Test water and a Test sample (a detergert) were added into the tester and it was operated to wash the glasses for 3 minutes. The glasses were then rinsed by test water for 1 minute and air-dried. The detergency of Test sample is evaluated.

The composition of test water and test conditions are as follows.

Test water:An aqueous solution obtained by dissolving calcium chloride (dihydrate, 59.0 mg/l) and magnesium chloride (hexahydrate, 27.2 mg/l) in distilled water Amount of water:700 ml Temperature of water:30±1° C. (both of washing water and rinsing water)

Rate of revolution of the tester: 250±10 rpm (iii) Method of evaluation of the detergency of the samples The slide glasses air-dried were washed with ethyl acetate to dissolve the stain, which are made up to a total volume of 100 ml. The absorbance of the obtained ethyl acetate washing was determined at the wave length of 500 nm and then the washing rate of the sample is calculated using the following equation.

$$\text{Washing rate (\%)} = 1 - \frac{\text{The absorbance of the ethyl acetate washing of the stain adhered slide glass after washing}}{\text{The absorbance of the ethyl acetate washing of the stain adhered slide glass before washing}} \times 100$$

2. Test results (i) Test samples 1 to 23 of the present invention and Comparative test samples prepared in Examples were subjected to the above washing test and all of washing rates of the test is 70% or more and higher than the value of the control without addition (washing rate 29%). The typical test results of Test samples are shown in Table 20 with those of Comparative test samples.

TABLE 20

| Sample | Molecular weight | Concentration (g/l) | Washing rate (%) |
| --- | --- | --- | --- |
| Test sample 3 | 16500 | 0.25 | 75 |
| Test sample 4 | 980 | " | 72 |
| Test sample 6 | 22000 | " | 72 |
| Test sample 7 | 15000 | " | 78 |
| Test sample 7 | " | 0.1 | 60 |
| Test sample 7 | " | 0.05 | 37 |
| Test sample 10 | 670 | 0.25 | 71 |
| Test sample 13 | 11800 | " | 78 |
| Test sample 22 | 24500 | " | 67 |
| Not added | — | — | 29 |
| Comparative test sample 13 | — | 0.25 | 33 |
| Comparative test sample 10 | — | " | 60 |
| Comparative test sample 10 | — | 0.1 | 46 |
| Comparative test sample 10 | — | 0.05 | 30 |
| Comparative | — | 0.25 | 34 |

TABLE 20-continued

| Sample | Molecular weight | Concentration (g/l) | Washing rate (%) |
|---|---|---|---|
| test sample 12 | | | |

(ii) A sample of a combination of Test sample 7 and Comparative test sample 10 (sucrose fatty acid ester) was tested in the same manner as in the above (i) and the test results are shown in Table 21.

TABLE 21

| Sample | Weight ratio | Concentration (g/l) | Washing rate (%) |
|---|---|---|---|
| Combination of | 1:4 | 0.1 | 62 |
| Test sample 7 | 1:1 | " | 74 |
| and Comparative test sample 10 | 4:1 | " | 70 |

(iii) Test sample 7, sodium dodecyl benzene sulfonate (DBS) and their combination were tested in the same manner as in the above (i) except for the use of a test water obtained by dissolving calcium chloride (dihydrate, 176 mg/l) and magnesium chloride (hexahydrate, 81.6 mg/l) in distilled water. The test results are shown in Table 22.

TABLE 22

| Sample | Concentration (g/l) | Washing rate (%) |
|---|---|---|
| Test sample 7 | 0.25 | 67 |
| DBS | 0.25 | 25 |
| Test sample 7 + DBS | 0.125 + 0.125 | 82 |
| | 0.20 + 0.05 | 79 |
| | 0.05 + 0.20 | 68 |

Note:
Comparative test samples in Tables 20 to 22 are the same ones as used in Test 7.

As seen from the above results, when a water of high hardness is used as a test water, the value of the washing rate of DBS which is an anior surface active agent is decreased, but when DBS is used together with Test sample 7, an excellent washing rate is observed.

It can be seen from the above results that the combined use has a remarkable synergistic effect.

(iv) A mixture of 1 part of the powder sample obtained by air-drying Test sample 7 and 4 parts of powdered soap was tested in the same manner as in the above (iii). It showed an excellent detergency and also insolubilization of the powder soap did not take place. On the other hand, when only the powdered soap was used, it was remarkably insolubilized, so that washing was impossible.

Test 17 (Drying and finishing effect after washing)

Thirty six transparent glass cups were dipped in commercially available milk, taken out of the milk and left for 30 minutes at room temperature. They were put into a rack and washed by 0.15% solution of a commercially available alkaline detergent at 60° C. for 4 minutes using the automatic washer MRK-NEWAMATIC JET WASHER LABO-200 from Mitamura Riken Kogyo Co., Ltd., JAPAN. Further the cups are rinsed by spraying on to them for 15 seconds a rinsing water which is an aqueous solution of following rinsing agents at 85° C. Immediately after rinsing, the cups were taken out of the washer, and the wetting state of their surface, the time required to dry them and the cleanness after drying were checked.

| Composition of rinsing agents | |
|---|---|
| Example (No. 1) | |
| Test sample 7 | 80% by weight |
| Propylene glycol | 20% by weight |
| Comparative test example (No. 2) | |
| Comparative test sample 10 | 8% by weight |
| Propylene glycol | 20% by weight |
| City water | 72% by weight |

The results are shown in Table 23.

TABLE 23

| Rinsing agent No. | Sample used | Concentration (Effective amount) (ppm) | Wetting state | Time required to dry | Cleanness |
|---|---|---|---|---|---|
| 1 | Test sample 7 | 50 | ○ | 2 to 3 minutes | ○ |
| 2 | Comparative test sample 10 | 50 | △ | 3 to 5 minutes | △ |
| | City water only | | X | More than 5 minutes | X |

Note:
Evaluation of wetting state
○ Being wet sufficiently
△ Being wet but insufficiently
X Ineffective
Evaluation of cleanness
○ Water spots are not observed.
△ Some water spots are observed but available.
X Unavailable.

Test 18 (Removing effect on agricultural chemicals from foods)

A) Method of preparing test samples for washing

The rind of an apple was cut to pieces approximately equal in thickness and size. They were fully washed with dilute hydrochloric acid and repeatedly with water, and dried to obtain clean pieces of the rind of an apple. Ten ppm of As in the form of $As_2O_3$ and DDT was accurately attached to the piece.

B) Washing

An 0.5% aqueous solution of a sample to be tested was prepared. A rind piece made in A) was washed in the solution at room temperature. After the piece was shaken for 5 minutes, it was put out of the solution and As and DDT washed down into the washing are determined.

C) Determination of removing rate of As

This was determined in accordance with the method for determining As in the note of the codex on food additives.

D) Determination of removing rate of DDT

This was determined in accordance with the method for determining chloride compounds in the note of the codex on food additives.

E) Evaluation of the results

⊙: Excellent in removal of the chemicals
   (a removing rate more than 80%)
○: Appearent in removal of the same
   (a removing rate of 50 to 80%)
△: Poor in removal of the same
   (a removing rate of 20 to 50%)

-continued

X: The same as in water washing in removal of the same (a removing rate less than 20%)

The results are shown in Table 24.

TABLE 24

| Sample | Removing rate of As | Removing rate of DDT |
|---|---|---|
| Test sample 7 | ⊚ | ⊚ |
| Test sample 22 | ⊚ | ○ |
| Comparative test sample 10 | ○ | ○ |
| Glycine (known detergent for agricultural chemicals) | ○ | Δ |

Note:
Comparative test sample used is the same one as used in Test 7.

Test 19 (Effect of dispersing or dissolving sparingly soluble surface active agents)

Twenty grams of each of sucrose fatty acid seters [trade name:DK ester F-160 (HLB15) and DK ester F-110 (HLB11) from DAI-ICHI KOGYO SEIYAKU CO., LTD., JAPAN] and soya bean lecithin [trade name:Honen Lecithin AY from Honen Seiyu Co., Ltd., JAPAN], which are sparingly soluble surface active agents, and a prescribed amount of a test sample in the form of powder were dispersed or dissolved in 200 g of water, and the resultant was spray-dried to obtain a preparation for testing.

Sucrose fatty acid ester was first moistened and mixed well with a small amount of water, then the required amount of water was added. The mixture was heated at a temperature of 60° C. to 80° C. to disperse the ester. Lecithin was dispersed in a prescribed amount of water.

Twenty grams of palmitic acid monoglyceride in the form of powder (trade name:Sunsoft No. 8001 from Taiyo Kagaku Co., Ltd., JAPAN) and a prescribed amount of a Test sample in the form of powder were mixed with a V type mixer to obtain a preparation for testing.

Ten grams of the preparations were added to a beaker containing 200 g of warm water water at 70° C. and the mixture was slowly stirred at 50 rpm using a magnetic stirrer to observe solubility of the preparation. The results are shown in Table 25.

TABLE 25

| Sample | Added Amount (g) | Surface Active agent | Evaluation |
|---|---|---|---|
| Test sample 1 | 5 | Sucrose fatty acid ester (HLB15) | ⊚ |
| 4 | 5 | Sucrose fatty acid ester (HLB15) | ⊚ |
| 6 | 5 | Sucrose fatty acid ester (HLB15) | ⊚ |
| 13 | 5 | Sucrose fatty acid ester (HLB15) | ⊚ |
| 16 | 5 | Sucrose fatty acid ester (HLB15) | ⊚ |
| 18 | 5 | Sucrose fatty acid ester (HLB15) | ⊚ |
| 19 | 5 | Sucrose fatty acid ester (HLB15) | ⊚ |
| 21 | 5 | Sucrose fatty acid ester (HLB15) | ⊚ |
| 23 | 5 | Sucrose fatty acid ester (HLB15) | ⊚ |
| 6 | 2 | Sucrose fatty acid ester (HLB15) | ○ |
| Blank | 0 | Sucrose fatty acid ester (HLB15) | X |
| Test sample 1 | 5 | Sucrose fatty acid ester (HLB11) | ⊚ |
| 6 | 5 | Sucrose fatty acid ester (HLB11) | ⊚ |
| Blank | 0 | Sucrose fatty acid ester (HLB11) | X |
| Test sample 1 | 5 | Palmitic acid monoglyceride (HLB3.5) | ⊚ |
| 4 | 5 | Palmitic acid monoglyceride (HLB3.5) | ⊚ |
| 6 | 5 | Palmitic acid monoglyceride (HLB3.5) | ⊚ |
| 13 | 5 | Palmitic acid monoglyceride (HLB3.5) | ⊚ |
| 16 | 5 | Palmitic acid monoglyceride (HLB3.5) | ⊚ |
| 18 | 5 | Palmitic acid monoglyceride (HLB3.5) | ⊚ |
| 19 | 5 | Palmitic acid monoglyceride (HLB3.5) | ○ |
| Test sample 21 | 5 | Palmitic acid monoglyceride (HLB3.5) | ○ |
| 23 | 5 | Palmitic acid monoglyceride (HLB3.5) | ○ |
| Blank | 0 | Palmitic acid monoglyceride (HLB3.5) | X |
| Test sample 1 | 5 | Palmitic acid Lecithin | ⊚ |
| 4 | 5 | " | ⊚ |
| 6 | 5 | " | ⊚ |
| 13 | 5 | " | ⊚ |
| 16 | 5 | " | ⊚ |
| 18 | 5 | " | ⊚ |
| 19 | 5 | " | ⊚ |
| 21 | 5 | " | ○ |
| 23 | 5 | " | ○ |
| Blank | 0 | " | X |

Evaluation
⊚: Uniformly dispersed or dissolved within 1 minute
○: Uniformly dispersed or dissolved
Δ: Producing a small number of massy globules
X: Producing a large number of massy globules Consideration It can be seen from the results shown in Table 25 that Test samples of the present invention can allow sucrose fatty acid ester, palmitic acid monoglyceride and lecithin to disperse or dissolve rapidly in water.

Test 20 (Test of particle dispersing property)

The following tests were conducted on Test samples prepared in Examples and Comparative test samples 10 (sucrose fatty acid ester), 11 (soya bean lecithin) and 15 (a polymer of sodium acrylate having a molecular weight of 8,000).

A. (Test of the property which decreases viscosity of calcium carbonate slurry)

Test method

A total weight 250 g of a Test sample and city water was put into the National M1 type mixer and then 250 g of calcium carbonate (light calcium carbonate from Takehara Kagaku Kogyo Co., Ltd., JAPAN) were added. The resultants was mixed for 2 minutes to obtain a 50% by weight slurry.

The slurry was transferred in a beaker and its viscosity was determined by using the DVH-B type viscometer from TOKYO KEIKI CO., LTD., JAPAN.

B. (Test of the property which decreases viscosity of kaolin slurry)

Test method

A total weight 200 g of a test sample and city water was put into the National MI type mixer and then 300 g of kaolin powder (Tsuchya Kaolin Kogyo Co., Ltd., JAPAN) were added and mixed for 2 minutes to make up 60 w/w% slurry.

The viscosity of caolin slurry was determined by the same manner as A.

C. (Test of the property which prevent sedimentation)

Test method 50 ml of 5.0 w/v% calcium carbonate (Takehara Kagaku Kogyo Co., Ltd., JAPAN, fine flurry) and a test sample were added into 100 ml calorimetric glass tube and filled up to 100 ml with water, served as test water.

After mixing well, the test water was left to stand for 5 minutes.

Test aliquot for Ca determination is sampled from the part of 50 ml position (at the middle part in height).

The dispersibility was calculated with Ca concentration before and after standing by following equation.

$$\text{Dispersion rate \%} = \frac{\text{The concentration of CaCO}_3 \text{ after standing}}{\text{The concentration of CaCO}_3 \text{ before standing}} \times 100$$

The results are shown in Table 26 wherein the blank spaces mean "not measured" or "not tested".

Test 21 (Effect on dispersibility of cocoa)

Test method

A prescribed amount of a Test sample was added to 5 g of a commercially available cocoa powder (Van Houten Cocoa containing 22 to 24% of cocoa butter). The mixture was fully mixed and poured into a 100 ml graduated cylinder containing 95 g of cold water at 5° C. The cylinder was turned upside down 20 times and then left for 10 minutes at room temperature. The portion of the added mixture which floats on the upper side was removed and its weight was measured.

The dispersibility of cocoa is calculated by the substract of floating weight from initial weight of cocoa, and expressed in percent of initial value.

TABLE 27

| Sample | Concentration (% by weight with respect to cocoa) | Dispersibility (%) |
|---|---|---|
| Example | | |
| Test sample 5 | 0.1 | 74 |
|  | 0.3 | 96 |
| Test sample 14 | 0.1 | 78 |
|  | 0.3 | 98 |
|  | 1.0 | 100 |
| Test sample 15 | 0.3 | 94 |
| Test sample 21 | 0.3 | 88 |
| Not added | — | 48 |
| Comparative example | | |
| Comparative test sample 10 | 0.1 | 52 |
|  | 0.3 | 67 |
| Comparative test sample 11 | 0.1 | 48 |
|  | 0.3 | 62 |
| Example | | |
| Test sample 14 + Comparative test | 0.08 + 0.02 | 84 |
|  | 0.05 + 0.05 | 88 |

TABLE 26

| Particle dispersing property | Test Sample* | | | | | | | | | |
|---|---|---|---|---|---|---|---|---|---|---|
|  | 1 | 2 | 3 | 4 | 5 | 6 | 7 | 10 | 11 | 12 |
| Calcium carbonate slurry (cps) | 291 | 30 (0.2%) 94 (0.1%) 396 | 1095 | 2920 | 48 (0.2%) 693 | 95 | 140 | 4700 | 382 | 1870 |
| Kaolin slurry (cps) | 4200 | 2246 | 331 | 1071 | 3800 | 67 (0.2%) 70 (0.1%) 97 | 82 | 1174 | 290 | 4800 |
| Sedimentation preventing property (%) (calcium carbonate) |  | 500 ppm 92 200 ppm 84 100 ppm 63 |  |  |  | 500 ppm 91 200 ppm 80 |  |  |  |  |

| Particle dispersing property | Test sample* | | | | | | | | | |
|---|---|---|---|---|---|---|---|---|---|---|
|  | 13 | 14 | 15 | 16 | 17 | 18 | 19 | 21 | 22 | 23 |
| Calcium carbonate slurry (cps) | 105 | 560 | 295 | 1510 | 72 | 210 | 252 | 357 | 329 | 720 |
| Kaolin slurry (cps) | 410 | 4200 | 95 | 159 | 2018 | 110 | 152 | 1052 | 191 | 898 |

| Particle-dispersing property | Comparative test sample* | | | |
|---|---|---|---|---|
|  | No. 10 | No. 11 | No. 15 | Blank |
| Calcium carbonate slurry (cps) | 5860 | >8000 | 150 | >8000 |
| Kaolin slurry (cps) | 4782 | >8000 | 180 | >8000 |
| Sedimentation preventing property (%) (calcium carbonate) | 1000 ppm 88 500 ppm 60 200 ppm 44 | | | |

*0.3% of the test sample was used for each case.

TABLE 27-continued

| Sample | Concentration (% by weight with respect to cocoa) | Dispersibility (%) |
|---|---|---|
| sample 10 | 0.02 + 0.08 | 68 |
| Test sample 14 + | 0.08 + 0.02 | 81 |
| Comparative | 0.05 + 0.05 | 85 |
| test sample 11 | 0.02 + 0.08 | 64 |

Consideration

It can be seen from the results of Table 27 that Test samples of the present invention are excellent dispersants which can improve the dispersibility of cocoa.

Further, a combination use of Test sample and sucrose fatty acid ester or soybean lecithin shows an excellent dispersibility of cocoa, and also a synergistic effect in the dispersibility.

Test 22

Each of Test samples of the present invention and Comparative test samples and a combination of them was dissolved in a prescribed amount of city water. To the solution was added 30 g of a liquid insecticide, Sumition (O,O-dimethyl O-4-nitro-m-tolyl phosphorothionate). The mixture was mixed for 10 minutes using a homomixer. Thus, the preparations 1–16 each having a weight of 100 g were obtained.

Test of stability

The preparation was put in a 50 ml measuring cylinder and left for stand at 60° C. for 4 weeks. The suspending rate showing stability of the preparation is obtained from the following equation.

$$\text{Suspending rate \%} = \frac{\text{Total height of the preparation} - \text{Height of the supernatant after standing}}{\text{Total height of the preparation}} \times 100$$

The conditions for preparation and the test results are shown in Table 28.

TABLE 28

| No. of preparation | Sample | Amount of the test sample (g) | Suspending rate (%) |
|---|---|---|---|
| 1 | Test sample 1 | 3 | 92 |
| 2 | " | 2 | 85 |
| 3 | " | 1 | 73 |
| 4 | Test sample 4 | 3 | 84 |
| 5 | Test sample 6 | 3 | 90 |
| 6 | Test sample 13 | 3 | 87 |
| 7 | Test sample 16 | 3 | 86 |
| 8 | Test sample 19 | 3 | 82 |
| 9 | Test sample 21 | 3 | 80 |
| 10 | Test sample 23 | 3 | 77 |
| 11 | Comparative test sample 10 | 3 | 63 |
| 12 | Comparative test sample 11 | 3 | 55 |
| 13 | Test sample 1 + Comparative test sample 11 | 0.2 + 0.8 | 72 |
| 14 | Test sample 1 + Comparative test sample 11 | 0.5 + 0.5 | 89 |
| 15 | Test sample 1 + Compartive test sample 11 | 0.8 + 0.2 | 78 |
| 16 | Not added | 0 | 52 |

Test 23

Each of Test samples of the present invention, Comparative test samples and a combination of them was dissolved in a prescribed amount of city water as in Test 22. The solution was put into a ball mill to which 15 g of MBTC (methylene bisthiocyanate) of a solid bactericide were added. Glass beads of 1 mm in diameter were put in the mill and the mixture was water-ground for 8 hours. Thus, the preparations 17 to 30 having a weight of 100 g each were obtained.

The stability tests on the preparations were conducted in the same manner as in Test 22. The results are shown in Table 29.

TABLE 29

| No. of preparation | Sample | Amount of test sample (g) | Suspending rate (%) |
|---|---|---|---|
| 17 | Test sample 6 | 3 | 91 |
| 18 | " | 1 | 82 |
| 19 | " | 0.5 | 70 |
| 20 | Test sample 13 | 3 | 88 |
| 21 | Test sample 16 | 3 | 85 |
| 22 | Test sample 19 | 3 | 78 |
| 23 | Test sample 21 | 3 | 76 |
| 24 | Test sample 23 | 3 | 73 |
| 25 | Not added | 0 | 30 |
| 26 | Comparative test sample 10 | 5 | 37 |
| 27 | Comparative test sample 11 | 5 | 45 |
| 28 | Test sample 6 + Comparative test sample 10 | 0.1 + 4 | 66 |
| 29 | Test sample 6 + Compartive test sample 10 | 0.25 + 0.25 | 85 |
| 30 | Test sample 6 + Compartive test sample 10 | 0.4 + 0.1 | 82 |

Each of 30 parts of Tsumacide (m-tolylmethylcarbamate, a powder insecticide) and 30 parts of DCPA (3',4'-dichloropropionanilide, a herbcide) was mixed with stirring with 5 parts of the sample obtained by drying Test sample 1 (the same Test sample as used in Test 8) and 65 parts of kaolin using a V type mixer to obtain two wettable preparation. Each of the wettable preparations was diluted with water at degree of dilution of 500, 1,000 and 2,000 folds. The portions of the diluted preparations were separately put in a 100 ml graduated cylinder and were left for 3 hours.

The states of them were observed and the dispersibility rates were calculated from the following equation.

$$\text{Dispersibility rate \%} = \frac{\text{Whole volume of the test preparation (ml)} - \text{Volume of the supernatant (ml)}}{\text{Whole volume of the test preparation (ml)}} \times 100$$

The values of the dispersibility of all the preparations were more than 80%.

Test 25

The preparations 31 to 47 each containing 5% by weight of Fenthion (O,O-dimethyl O-4-methylthio-m-tolylphosphrothionate, a liquid nsecticide) and having a weight of 100 g were prepared in the similar manner as in Test 21 using Fenthion instead of Sumition.

Test of stability

The preparation was left at 50° C. for one month. The decomposition rate of the insecticide in the preparation was determined by measuring the change of the concentration of the insecticide caused by the preparation being left.

The insecticide in the preparation was determined using a FPD gaschromatograph. The results are shown in Table 30.

TABLE 30

| No. of preparation | Sample | Amount of sample (g) | Decomposition rate (%) |
|---|---|---|---|
| 31 | Test sample 5 | 1 | 1.8 |
| 32 | " | 0.5 | 2.6 |
| 33 | Test sample 4 | 1 | 3.7 |
| 34 | Test sample 6 | 1 | 2.4 |
| 35 | " | 0.5 | 4.7 |
| 36 | Test sample 13 | 1 | 2.8 |
| 37 | Test sample 16 | 1 | 2.6 |
| 38 | Test sample 19 | 1 | 4.8 |
| 39 | Test sample 21 | 1 | 5.2 |
| 40 | Test sample 23 | 1 | 6.6 |
| 41 | Comparative test sample 10 | 2 | 25.0 |
| 42 | Comparative test sample 11 | 2 | 30.0 |
| 43 | Test sample 1 + Comparative test sample 11 | 0.1 + 0.4 | 4.0 |
| 44 | Test sample 1 + Comparative test sample 11 | 0.25 + 0.25 | 1.7 |
| 45 | Test sample 1 + Comparative test sample 11 | 0.4 + 0.1 | 2.2 |
| 46 | Test sample 1 + Comparative test sample 10 | 0.25 + 0.25 | 2.1 |
| 47 | Not added | 0 | 36.0 |

Test 26

2l of a 2000 ppm aqueous solution of each of Test samples of the present invention and such conventional surface active agents as sodium dodecylbenzenesulfonate, lauryltrimethylammonium chloride and polyoxyethylenenonylphenylether (n=10) were separately sprayed to a young seedling of tomato grown for about 25 days after seeding. The young seedlings were kept in a humid atmosphere for six days and the degree of damage of them from the sprayed agent was observed. The results are shown in Table 31.

Test samples used are the ones desalted and drided as in Test 24.

TABLE 31

| Sample | Degree of damage of young tomato seedlings |
|---|---|
| not added | — |
| Test sample 6 | — |
| Test sample 13 | — |
| Test sample 16 | — |
| Test sample 21 | — |
| Sodium dodecylbenzenesulfonate | ± |
| Lauryltrimethylammonium chloride | + + |
| Polyoxyethylene-nonylphenylether (n = 10) | + |

Note
—: No damage.
±: The edges of some leaves died.
+: Some leaves changed color to brown.
+ +: Many leaves changed color to brown.

Analytical results of Test samples

Amino acid compositions of the test samples 1, 7, 13 and 15 were determined. The results are shown in Table 32. Each of the values in Table 32 represents number of grams of the amino acids contained in 100 g of the corresponding Test sample.

TABLE 32

| Amino acid | Test sample | | | |
|---|---|---|---|---|
| | No. 1 | No. 7 | No. 13 | No. 15 |
| Arginine | 1.2 | <0.1 | <0.1 | 0.1 |
| Lysine | 0.7 | 0.8 | 0.9 | 3.6 |
| Histidine | 1.4 | 1.5 | 1.2 | 1.6 |
| Phenylalanine | 4.0 | 3.7 | 4.6 | 3.4 |
| Tyrosine | 2.6 | 2.4 | 3.7 | 2.6 |
| Leucine | 5.2 | 5.1 | 12.1 | 5.4 |
| Isoleucine | 2.8 | 2.4 | 2.4 | 2.6 |
| Methionine | 1.2 | 1.1 | 1.6 | 0.9 |
| Valine | 3.1 | 3.1 | 3.2 | 3.4 |
| Alanine | 2.1 | 2.3 | 6.4 | 3.4 |
| Glycine | 2.6 | 3.0 | 2.4 | 3.6 |
| Proline | 10.5 | 8.4 | 7.1 | 3.7 |
| Glutamic acid | 27.7 | 26.4 | 15.5 | 11.9 |
| Serine | 3.4 | 1.4 | 1.2 | 1.1 |
| Threonine | 1.9 | 0.7 | 0.6 | 0.7 |
| Aspartic acid | 2.7 | 2.5 | 4.3 | 7.7 |
| Tryptophan | 0.7 | 0.7 | 0.3 | 0.9 |
| Cysteine | 0.6 | 0.5 | 0.4 | 0.3 |

Figure 2A:
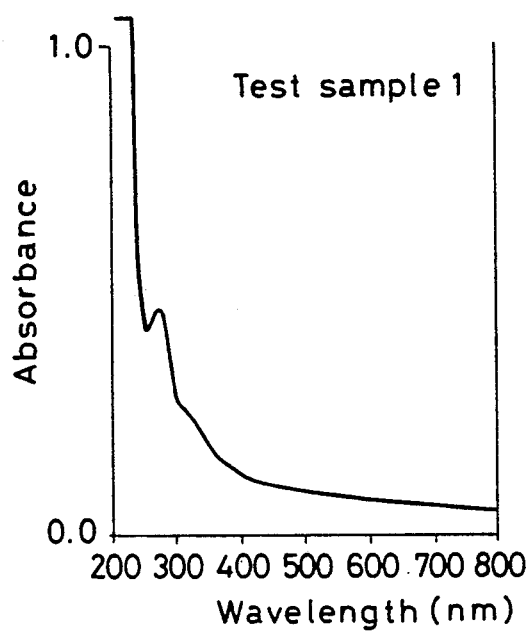
Figure 2B:
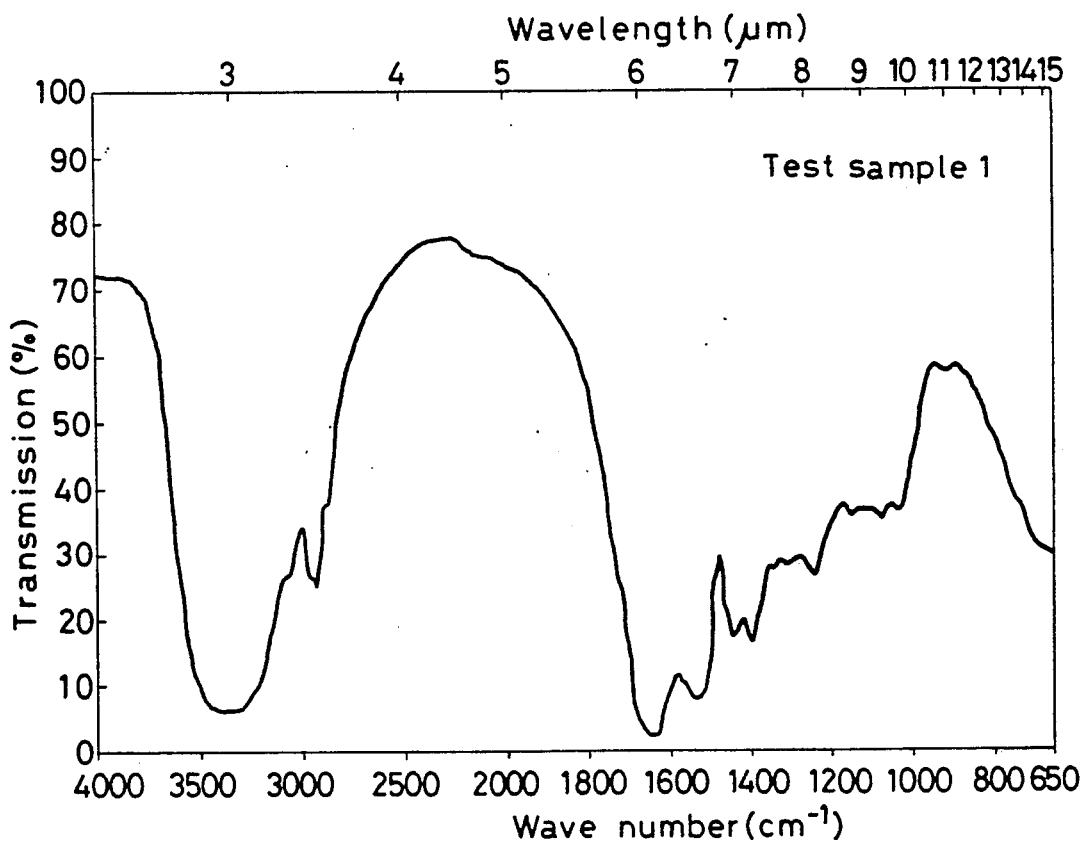
Figure 3A:
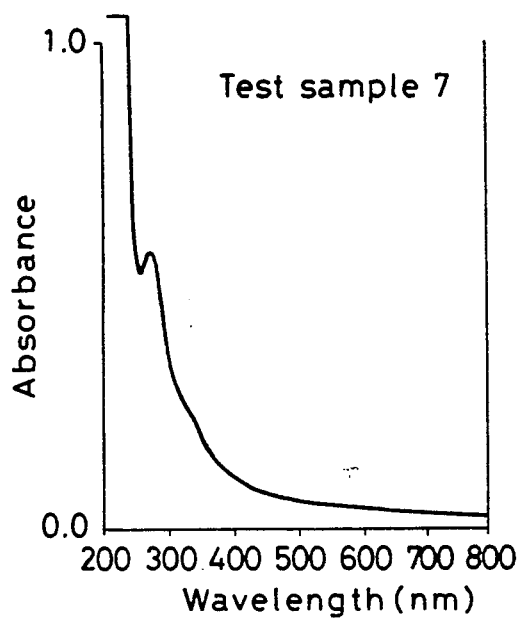
Figure 3B:
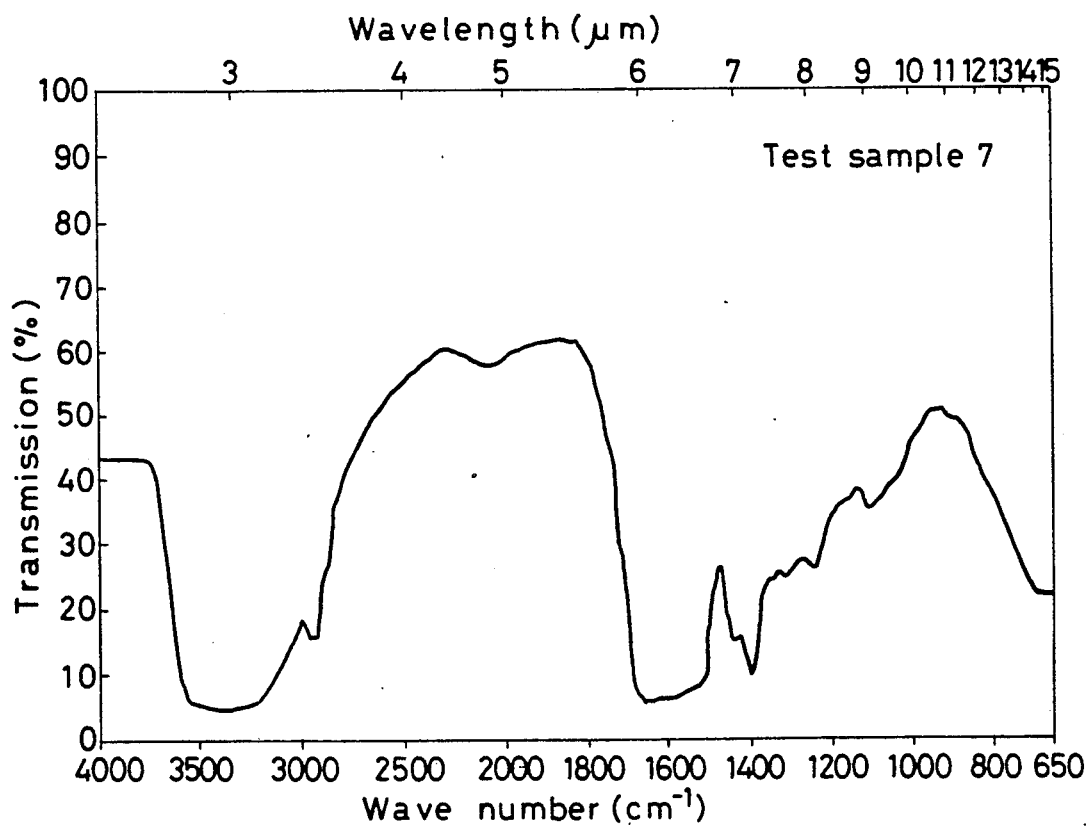
Figure 4A:
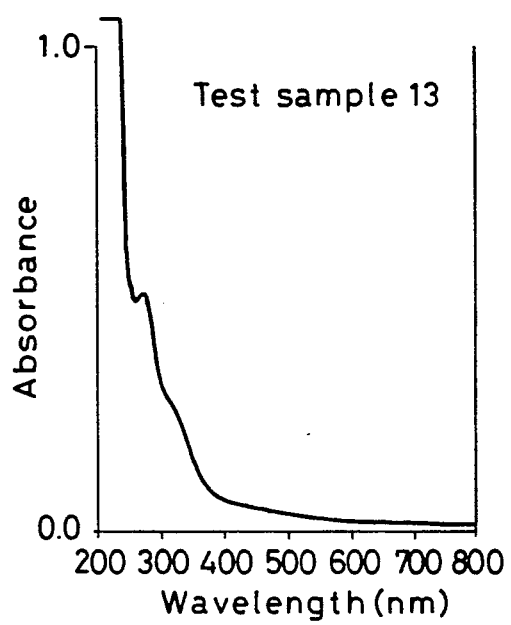
Figure 4B:
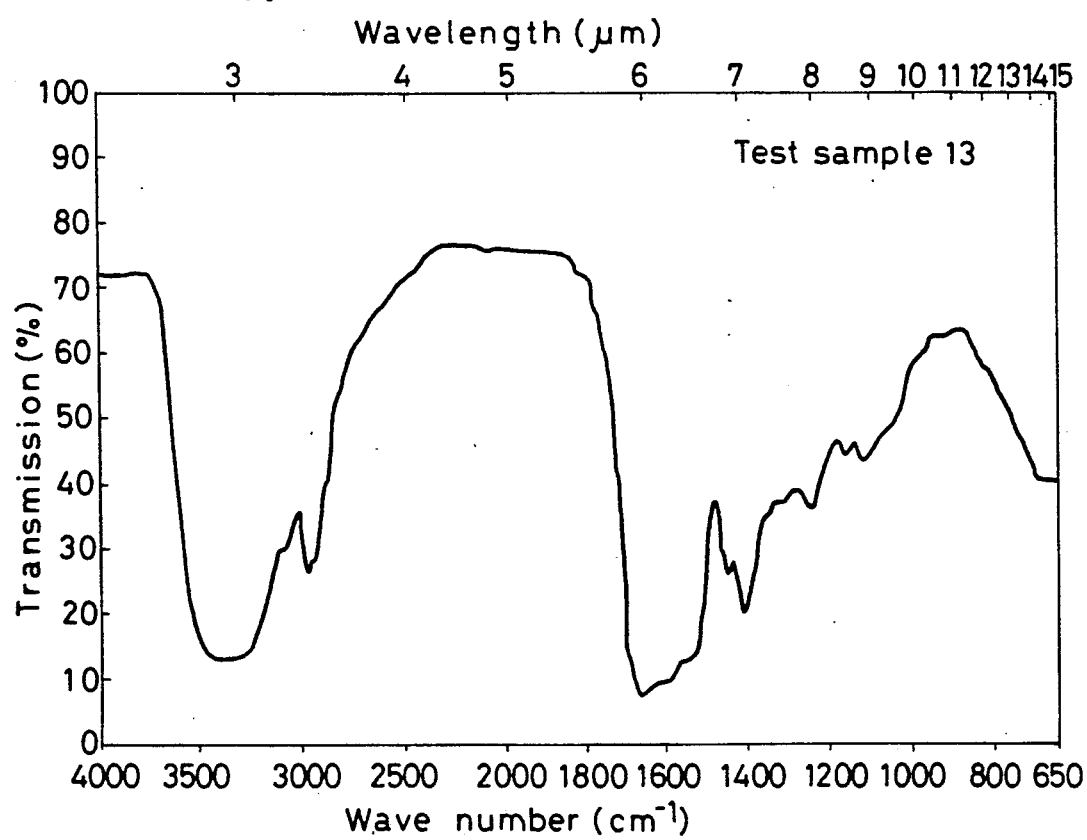
Figure 5A:
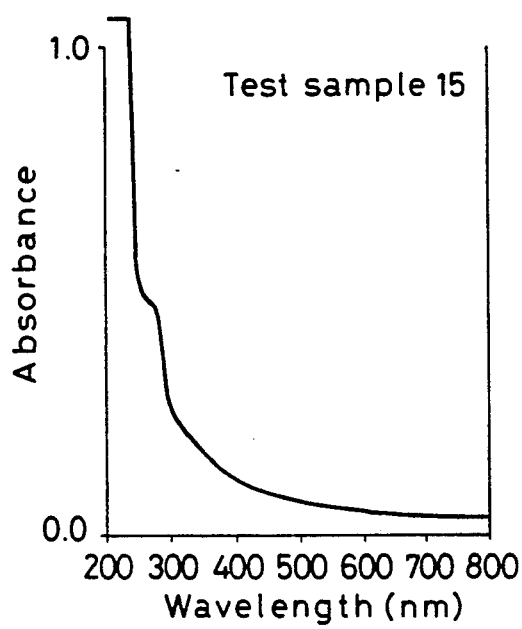
Figure 5B:
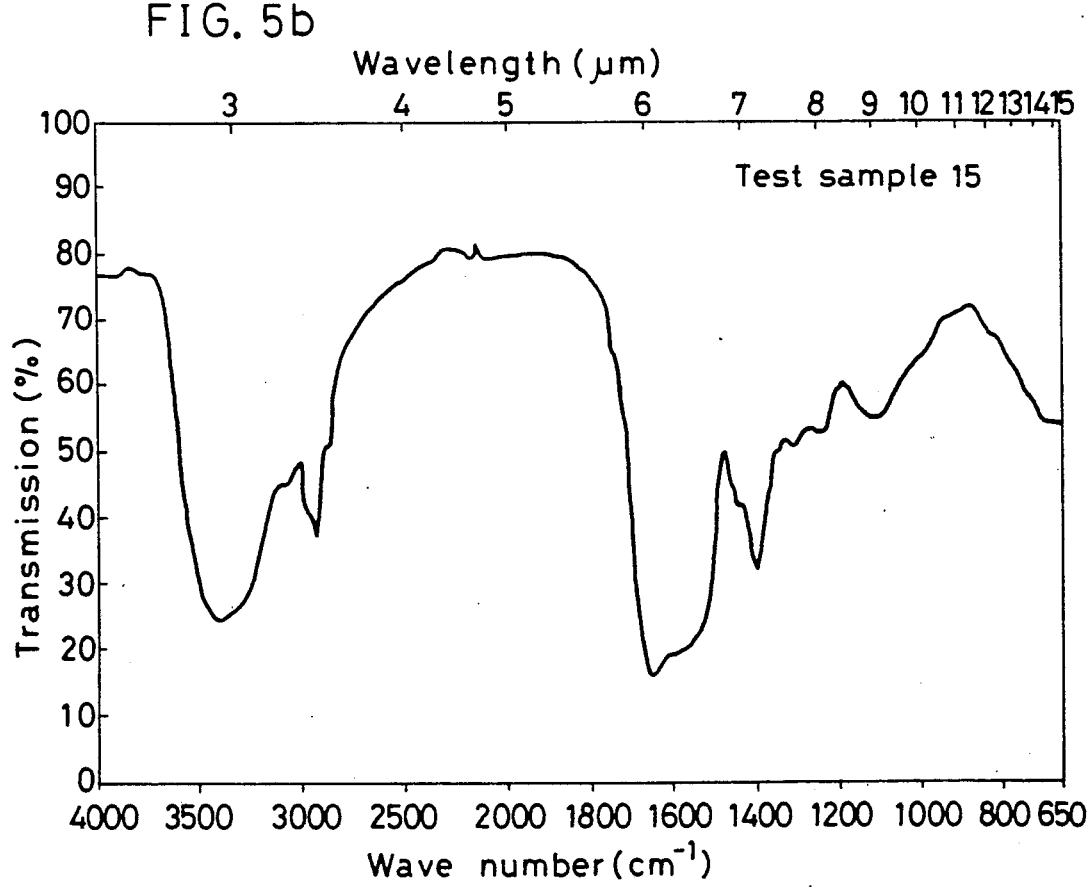

The ultraviolet and visible light absorption spectrums of Test samples 1, 7, 13 and 15 are shown in FIGS. 2a, 3a, 4a and 5a, respectively and the infrared light absorption spectrums of the same samples are shown in FIGS. 2b, 3b, 4b, and 5b, respectively.

What we claimed is:

1. A protein partial degradation product that is derived from a grain protein selected from the group consisting of wheat gluten, maize, gluten, soya bean protein, and combinations of the foregoing, wherein the protein partial degradation product is a powder characterized by:

(a) a weight average molecular weight (according to the Gel filtration method) of from 670–79,000;

(b) an ultraviolet absorption λmax of from about 260 to about 280 nm and an infrared absorption of about 1400, 1630, and 3400 cm$^{-1}$;

(c) an isoelectric point of from about pH 3.9 to about pH 5.0;

(d) a buffering action such that 2-25 ml of 1N-hydrochloric acid is required to lower the pH of 100 ml of a 5% by weight aqueous solution of the protein partial degradation product from 6 to 2;

(e) solubility in water and insolubility in methanol, ethanol, acetone and ethyl ether;

(f) a pale yellow to red brown color;

(g) showing coloration Xanthoprotein reaction and Ninhydrin reaction;

(h) a surface tension-reducing capacity such that the surface tension of pure water at 25° C. is reduced to 50 dyne/cm or less, as measured by du Noiiy's tensiometer, by adding 0.1% by weight of the protein partial degradation product to the pure water; and (i) an emulsifying capacity such that 100 g of a mixture of water and soya bean oil, containing at least 30% by weight of soya bean oil, can be emulsified completely for not less than 20 minutes by adding 1 g. of the protein partial degradation product to the mixture.

2. The product of claim 1 wherein the weight average molecular weight is from 700–70,000.

3. The product of claim 1 wherein the weight average molecular weight is from 17,000–70,000.

4. The product of claim 1 wherein the emulsifying capacity is such that 100 g of a mixture o water and soya bean oil, containing at least 30% by weight of soya bean oil, can be emulsified completely for not less than one hour by adding 1 g. of the protein partial degradation product to the mixture.

5. A protein partial degradation product that is derived from a grain protein selected from the group consisting of wheat gluten, maize gluten, soya bean gluten, and combinations of the foregoing, wherein the protein partial degradation product is a powder characterized by:

(a) a weight average molecular weight (according to the Gel filtration method) of from 670–79,000;

(b) an ultraviolet absorption λmax of from about 260 to about 280 nm and an infrared absorption of about 1400, 1630, and 3400 $cm^{-1}$;

(c) an isoelectric point of from about pH 3.9 to about pH 5.0;

(d) a buffering action such that 2–25 ml of 1N-hydrochloric acid is required to lower the pH of 100 ml of a 5% by weight aqueous solution of the protein partial degradation product from 6 to 2;

(e) solubility in water and insolubility in methanol, ethanol, acetone and ethyl ether;

(f) a pale yellow to red brown color;

(g) showing coloration Zanthoprotein reaction and Ninhydrin reaction;

(h) a surface tension-reducing capacity such that the surface tension of pure water at 25° C. is reduced to 50 dyne/cm or less, as measured by du Noiiy's tensiometer, by adding 0.1% by weight of the protein partial degradation product to the pure water; and (i) an emulsifying capacity such that 100 g of a mixture of water and soya bean oil, containing at least 30% by weight of soya bean oil, can be emulsified completely for not less than 20 minutes by adding 1 g. of the protein partial degradation product to the mixture, wherein the protein partial degradation product is produced by a process comprising subjecting the grain protein to a multi-step degradation treatment comprising a combination of (i) a hydrolysis treatment with alkali, and (ii) one or more degradation treatments with an acid, enzyme, oxidizing agent or reducing agent.

6. The product of claim 5 wherein the weight average molecular weight is from 700–70,000.

7. The product of claim 5 wherein the weight average molecular weight is from 17,000–70,000.

8. The product of claim 5 wherein the emulsifying capacity is such that 100 g of a mixture of water and soya bean oil, containing at least 30% by weight of soya bean oil, can be emulsified completely for not less than one hour by adding 1 g. of the protein partial degradation product to the mixture.

* * * * *

UNITED STATES PATENT AND TRADEMARK OFFICE
CERTIFICATE OF CORRECTION

PATENT NO. : 5,138,038
DATED : August 11, 1992
INVENTOR(S): KATAYAMA et al.

It is certified that error appears in the above-identified patent and that said Letters Patent is hereby corrected as shown below:

In claim 1, Column 44, line 37: After "maize", delete --,--.

In claim 4, Column 45, line 6: Change "mixture o water" to --mixture of water--.

In claim 5, Column 46, line 1: Change "Zanthoprotein" to --Xanthoprotein--.

Signed and Sealed this

Twenty-third Day of November, 1993

Attest:

BRUCE LEHMAN

Attesting Officer          Commissioner of Patents and Trademarks